US011567056B2

(12) United States Patent
Smith

(10) Patent No.: US 11,567,056 B2
(45) Date of Patent: Jan. 31, 2023

(54) METHODS FOR EVALUATING ROCK PROPERTIES

(71) Applicant: Michael Smith, Tulsa, OK (US)

(72) Inventor: Michael Smith, Tulsa, OK (US)

(*) Notice: Subject to any disclaimer, the term of this patent is extended or adjusted under 35 U.S.C. 154(b) by 3 days.

(21) Appl. No.: 17/019,130

(22) Filed: Sep. 11, 2020

(65) Prior Publication Data

US 2020/0408732 A1     Dec. 31, 2020

Related U.S. Application Data

(63) Continuation of application No. PCT/US2019/022362, filed on Mar. 14, 2019.

(60) Provisional application No. 62/643,132, filed on Mar. 14, 2018.

(51) Int. Cl.
| | | |
|---|---|---|
| *G01N 33/24* | (2006.01) | |
| *E21B 49/00* | (2006.01) | |
| *E21B 49/02* | (2006.01) | |

(52) U.S. Cl.
CPC ......... *G01N 33/241* (2013.01); *E21B 49/005* (2013.01); *E21B 49/02* (2013.01)

(58) Field of Classification Search
CPC ...... G01N 33/241; E21B 49/005; E21B 49/02
See application file for complete search history.

(56) References Cited

U.S. PATENT DOCUMENTS

| | | | | |
|---|---|---|---|---|
| 5,224,658 A | * | 7/1993 | Smith | G01N 1/286 241/94 |
| 5,241,859 A | * | 9/1993 | Smith | G01N 33/241 356/128 |
| 5,286,651 A | | 2/1994 | Smith | |
| 5,328,849 A | * | 7/1994 | Smith | G01N 33/241 436/25 |

(Continued)

FOREIGN PATENT DOCUMENTS

| | | | | |
|---|---|---|---|---|
| CA | 2068012 | | 12/1992 | |
| CA | 2469804 C | * | 7/2010 | ........... E21B 49/005 |

(Continued)

OTHER PUBLICATIONS

Jorge, et al., "Analysis of Volatiles in Fluid Inclusions by Direct online Crushing Mass Spectrometry", Journal of Brazilian Chemical Society, 22.3, 2011; 437-455, p. 445, col. 1 [online] URL<http://www.scielo.br/pdf/jbchs/v22n3/V22n3a05.pdf>.

(Continued)

*Primary Examiner* — John Fitzgerald
(74) *Attorney, Agent, or Firm* — Transformative Legal LLC; Len S. Smith; Megan J. Butts

(57) ABSTRACT

Methods of analyzing the rock content of a geologic formation are provided herein. The methods typically comprise obtaining samples from the formation and subjecting the samples to conditions that will cause the extraction and/or release of one or more volatile compounds from the samples, if present in the samples, and then analyzing the amount of such one or more volatile compounds released/extracted (Continued)

from the sample and then further relating such results to the physical and/or rock content composition of two or more regions of the geologic formation. The results can be used to inform or guide oil and/or gas exploration and/or production operations, such as placement of fracking operations.

10 Claims, 19 Drawing Sheets

(56) References Cited

U.S. PATENT DOCUMENTS

| | | | | |
|---|---|---|---|---|
| 5,416,024 | A * | 5/1995 | Smith | G01N 33/241 850/16 |
| 6,661,000 | B2 | 12/2003 | Smith et al. | |
| 7,210,342 | B1 | 5/2007 | Sterner et al. | |
| 7,395,691 | B2 * | 7/2008 | Sterner | E21B 21/01 73/152.19 |
| 10,190,413 | B2 * | 1/2019 | Smith | H01J 49/0468 |
| 10,260,336 | B2 * | 4/2019 | Smith | G01N 1/24 |
| 10,494,919 | B2 * | 12/2019 | Smith | G01N 3/12 |
| 11,236,020 | B2 * | 2/2022 | Haque | C04B 28/006 |
| 11,280,186 | B2 * | 3/2022 | Smith | H01J 49/0422 |
| 2003/0106995 | A1 * | 6/2003 | Smith | G01N 33/241 250/282 |
| 2004/0099804 | A1 | 5/2004 | Liu et al. | |
| 2018/0195383 | A1 * | 7/2018 | Smith | G01N 3/08 |
| 2018/0306031 | A1 * | 10/2018 | Smith | G01N 3/12 |
| 2018/0319708 | A1 * | 11/2018 | Haque | C04B 28/00 |
| 2018/0355717 | A1 * | 12/2018 | Smith | H01J 49/0422 |
| 2021/0207477 | A9 * | 7/2021 | Smith | E21B 49/081 |
| 2021/0215652 | A1 * | 7/2021 | Smith | G01N 33/004 |

FOREIGN PATENT DOCUMENTS

| | | | | |
|---|---|---|---|---|
| GB | | 2256885 A * | 12/1992 | G01N 33/241 |
| WO | WO-2012055009 A1 * | | 5/2012 | C10G 1/04 |
| WO | WO-2018111945 A1 * | | 6/2018 | E21B 49/005 |

OTHER PUBLICATIONS

McCarthy, Kevin et al., "Basic Petroleum Geochemistry for Source Rock Evaluation", Oilfield Review, 23.2, 2011.

International Search and Written Opinion for PCT/US2019/22362 dated Aug. 5, 2019.

* cited by examiner

Close-up Comparison of Two Cuttings Photographs showing heterogeneity among the samples.
Oil Shale Lateral

METHODS FOR EVALUATING ROCK PROPERTIES

CROSS-REFERENCE TO RELATED APPLICATIONS

This application claims priority to U.S. Provisional Patent Application No. 62/643,132, filed Mar. 14, 2018 and is a continuation of International Application number PCT/US2019/022362, filed Mar. 14, 2019, both of which are hereby incorporated by reference.

FIELD OF THE INVENTION

This invention relates to the analysis and characterization of materials, especially rocks, and the use of information obtained through such analyses, such as in planning petroleum production operations.

BACKGROUND OF THE INVENTION

The recent oil and gas shale revolution in the United States and elsewhere is based on producing oil and gas by fracking long horizontal wells. These horizontal wells are typically 1 to 2 miles (about 1.6-3.2 km) long and are typically drilled their entire length within a single formation, often staying the entire length within a single unit of a single formation, often of only 5 feet (about 1.5 m) in thickness. Usually a horizontal well is fracked and tested within a week to a month or a few months after drilling the horizontal well.

The intent of these horizontal wells is to produce large volumes of oil and gas charged strata. The wells typically have a fracking radius of 100 to 200 feet. Thus, fracking is not only the unit that the horizontal wells are drilled in, but also a significantly larger area of overlying and underlying strata.

Even within a single 5-foot (5') unit in a single formation there can be considerable changes in rock properties (with respect to any other part of the formation), and these changes in rock properties can affect the ultimate oil and gas production economics of a horizontal well either positively or negatively.

In vertical wells, rock properties are often attempted to be in part derived from wire line logs. The 3 main logs routinely used are resistivity, gamma ray, and sonic logs. Other similar logs may also be employed for this purpose. Generation of these logs add significant costs to a vertical well operation. However, the costs of running these logs in horizontal wells are so high as to usually be prohibitive. Also, the quality of these logs in horizontal wells are generally recognized as being not of as high quality as they are in vertical wells.

Sometimes rock properties in vertical wells are studied using core samples ("cores"). However, cores cannot be taken in horizontal wells, and even in vertical wells they are extremely expensive to drill and collect and analyze. Also coring usually causes the drilling of the well to take much more time than drilling a normal well. And receiving the results of the core analyses can often take months.

I have previously invented methods comprising extracting volatile compounds from materials associated with geologic formations, such as petroleum drill cuttings from a petroleum exploration or production site and relating such volatile compound information to the oil content of formations. These methods are described in International Patent Application WO 2018/11194 and U.S. Pat. No. 10,190,413, which issued from a counterpart US patent application. My inventions described in WO 2018/111945 include identification of "trapped" oil deposits, which I indicate were captured by surrounding impermeable rock. Outside of this characterization, however, it was not known to me or others prior to the invention described herein that such volatile compounds could also or alternatively be used to characterize the properties of rocks in a formation, especially in a region associated with a single oil deposit, and to identify geologic features of the formation, such as faults, therein.

BRIEF SUMMARY OF THE INVENTION

This invention provides a variety of methods for evaluating the rock characteristics of geologic formations. In one aspect of the invention the geologic formation is a petroleum deposit-associated formation. The formation can include a single deposit or multiple deposits. The deposit or deposits in such geologic formations typically will have the same or at least substantially similar characteristics—e.g., in terms of grade of oil, chemical composition, etc.

In one aspect, the invention provides a method of characterizing rock content of a geologic formation, and to use such information for related activities such as directing petroleum drilling operations, comprising (a) obtaining a number of samples of rock from the different portions of a geologic formation, (b) subjecting the rock samples to conditions that cause the release of detectable amounts of benzene and toluene from the rock samples, if present in the rock samples, (c) analyzing the amount of benzene and toluene released from the rock samples, and (d) calculating the ratio of toluene to benzene released from the rock samples to characterize the rock properties of the formation. I have discovered that relatively high toluene-to-benzene ratios, such as a minimum ratio of at least about 4.5 to 1, are indicative of parts of formations that typically have important physical properties, and very often are associated with natural fault formations in the formation. This information can be used to direct petroleum production operations (e.g., drilling, fracking, and/or other operations) to one or more locations identified as being associated with a desired minimum toluene-to-benzene ratio. In some cases, the minimum toluene-to-benzene ratio is set to at least about 6 to 1. In other cases, the minimum toluene-to-benzene ratio is at least about 9 to 1. The extraction of toluene and benzene can be performed by any suitable method, such as the methods described in WO 2018/11194. In one aspect, the method is performed by subjecting the samples to a single set of conditions to release only one aliquot of volatile compounds from each sample (e.g., the method is performed using a "single aliquot" method such as described therein). The samples can comprise and often will be mostly composed of, if not at least 90%, at least 95%, or more composed of drill cuttings, such as petroleum drill cuttings produced in exploration and/or production wells in the formation. As exemplified and discussed below, an advantageous aspect of the invention comprises performing the method in horizontal petroleum wells (wells in which the orientation of the well is horizontal in orientation, i.e., predominately more parallel to the surface of the earth).

In another aspect, the invention provides a method of identifying areas of different rock properties in a petroleum-associated geological formation comprising (a) obtaining a plurality of rock samples obtained from different portions of a geological formation associated with a petroleum deposit having at least substantially uniform properties, (b) subjecting the rock samples to conditions that cause the release of detectable amounts of one or more volatile compounds from the rock samples, if present in the rock samples, (c) analyzing the amount of the one or more volatile compounds released from the rock samples, and (d) determining if there is a minimum difference in the release of at least one of the released volatile compounds, such as a difference of at least about 50% in the amount of at least one of the released volatile compounds, obtained from a first sample area from at least one sample obtained from a second sample area. An advantage of the method is that it can detect differences in rock properties of the formation even when the entirety of the formation has been determined to be associated with a single oil deposit or a number of oil deposits have identical or substantially uniform conditions (e.g., in terms of oil grade, chemistry, etc.). Those skilled in the art will understand when petroleum has substantially uniform properties. In general, certain formations are known to be associated with oil deposits that reflect overall similar or identical properties throughout various areas of the formation/well (vertically and/or horizontally). In such cases, I have discovered that the differences in volatile compounds released from such compounds by application of gentle vacuum and other methods described in my prior patent application are likely also, primarily, or essentially entirely associated with the properties of the rocks that make up the formation and/or the physical properties of the formation (such as the presence of natural faults). As will be clear from this disclosure, such properties are, however, often indicative of the areas of the well/formation to produce petroleum (e.g., the presence of a fault identifies an area that can be associated with relatively high and easy production as compared to other areas). Also or alternatively, an advantage of the method is identification of regions of different rock properties where other commonly used analytical methods, such as gamma ray logs and resistivity logs, provide little or no indication that there is a difference in the characteristics of the rocks in the formation. Thus, for example, the method can indicate that there is a minimum difference in the release of volatile compounds from two or more portions of the formation but the gamma ray log data and/or resistivity log data associated with the two or more areas do not reflect a difference of more than about 10%, more than about 15%, more than about 20%, more than about 25%, or more than about 30% (e.g., more than about 50%, more than about 75%, or more than about 100% or even more than about 150%), with respect to each other. Another advantageous aspect of the method is that it can, in some embodiments, be used to identify differences in relatively small areas, such as areas of about 100 meters or less in one or more directions, about 50 meters or less in one or more directions, about 30 meters or less in one or more directions or even small areas (e.g., areas of about 20 meters or less in one or more directions, about 15 meters or less in one or more directions, about 10 meters or less in one or more directions, about 7 meters or less in one or more directions, about 3 meters or less in one or more directions, or even about 2 meters or less in one or more directions).

In yet another aspect, the invention provides methods of identifying areas of different rock properties in a geologic formation associated with an oil deposit comprising (a) obtaining a plurality of rock samples obtained from different portions of a geological formation associated with a petroleum deposit having at least substantially uniform properties, (b) subjecting the rock samples to conditions that cause the loss of petroleum from the rock samples, (c) subjecting the rock samples to conditions that cause the release of detectable amounts of one or more volatile compounds associated with petroleum from the rock samples, if present in the rock samples, (c) analyzing the amount of the one or more petroleum-associated volatile compounds released from the rock samples, wherein the presence of a relatively high concentration of petroleum-associated volatile compounds in the samples is indicative of rock having relatively poor petroleum production properties. Similar to other aspects of the invention, such information can be used to, for example, direct oil production operations, such as drilling operations or fracking operations, in an area associated with having an amount of petroleum-associated volatile compounds that are indicative of favorable conditions for oil production. Similar to the permeability determination methods I have invented and described in WO 2018/11194 this method is counter-intuitive in that the identification of less petroleum-associated compounds in the rock is indicative of more favorable petroleum production capabilities. This is because the retention of petroleum in such rocks after being subjected to conditions in which petroleum materials are typically lost from the samples (either long term exposure to environmental conditions or exposure to "active" conditions such as heating, crushing, and the like) means that the rock has one or more properties that cause the rock to retain the petroleum, rather than release it, indicating that petroleum flow and release from such rock will be relatively poor and less economically rewarding. A key difference with the method described herein with respect to such permeability methods is that the method can be performed using a single set of conditions for the release of volatile compounds (e.g., use of single aliquots obtained by the methods described in WO 2018/11194).

As described below the methods of the invention can be advantageously performed to identify differences in the characteristics of rocks to identify differences even when such differences are not detectable by regular visual inspection (with the naked eye).

BRIEF DESCRIPTION OF THE DRAWINGS/FIGURES

FIG. 1 is a log of select volatile chemical compounds obtained from washed and dried petroleum drill cuttings that were analyzed by rock volatiles analyses for a first well analyzed as an exemplary application of the inventive methods described herein.

FIG. 2 provides the same plot of data as FIG. 1 with certain areas highlighted to aid in illustrating the data.

FIG. 3 is a photo-mosaic showing washed and dried cuttings from the horizontal well that was the source of the cuttings that led to the data shown in FIGS. 1 and 2. Within a row the depths increase from left to right. Vertically the depths increase from top to bottom.

DETAILED DESCRIPTION OF THE INVENTION

Figure 1:
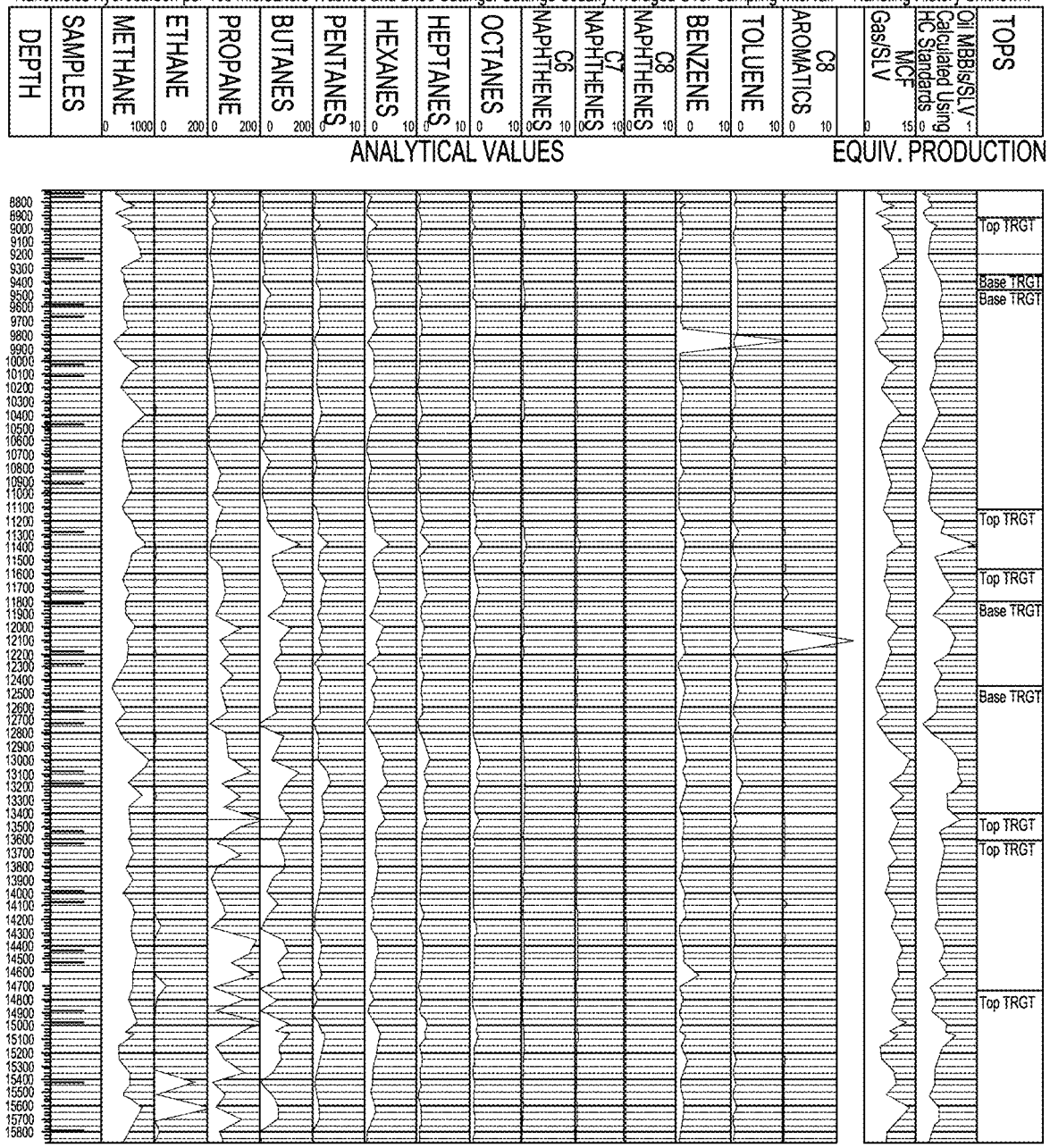

The changes in rock properties within a horizontal well can have a major economic impact on that well. This insight has led me to recognize that there is a need for reliable tools that can allow one to determine the location of rocks having similar or dissimilar properties in strata drilled by horizontal wells of reasonable expense and reasonable turnaround time. The invention described herein fulfills this objective by providing a variety of methods that can be used to characterize rock properties of geologic formations, such as petroleum well sites.

The methods and devices described in my prior patent application PCT/US2017/65921 (published as WO 2018/111945), filed Dec. 12, 2017 ("the '921 application") are relevant to and useful in practicing the invention described herein. Accordingly, the '921 application is hereby incorporated in its entirety herein. The methods described in my other patent application (U.S. Provisional Patent Application No. 62/634,794, filed Feb. 23, 2018), also may be advantageously practiced in some respects with various methods described herein, and, accordingly, the '794 application is likewise incorporated herein in its entirety.

I have invented a method of mapping the above-described dissimilar rock properties found within rock formations by obtaining samples of rock materials, which can, in one aspect, be conveniently obtained in the form of petroleum drill cuttings (in general these methods also may be applied directly to rock formations, but for sake of practicality and affordability the focus of this disclosure is on the use of samples). As described in the incorporated '921 application (e.g., in paragraph [0038] as published), the samples selected for analysis in the performance of the method can comprise, are substantially comprised of (i.e., more than about 20% of the samples are), are primarily comprised of (i.e., more than 51% of the samples are), consist essentially of (are comprised of to a level that the amount of non-conforming material does not impact the nature of the total sample or sample set), or consist entirely of, material that substantially lack relevant fluid inclusions ("RFIs"). As defined therein, "RFIs" in the context of the invention refers to fluid inclusions that (1) contain one or more materials that are indicative of the presence of a substance in the material (at least in the inclusions), such as petroleum or petroleum-related substances (e.g., organic acids, hydrocarbons, and the like, such as acetic acid) and (2) the presence of such materials reflect the present condition of the material (in terms of the presence of the target substance). As further described in the incorporated '921 application (e.g., in paragraph [0157] as published), samples can primarily or entirely contain non-fluid inclusion volatile substances. In one aspect, the method comprises applying the volatile compound extraction, capture, and detection methods I invented and described in the '921 application to such samples, so as to release volatile compounds and to use such released volatile compounds to determine the rock properties of the samples, and accordingly, the properties of the area under study. In aspects, as described in the incorporated '921 application (e.g., in paragraph [0102] as published), the methods of the invention can comprise analysis of a single aliquot, for example a single aliquot obtained under gentle/low vacuum conditions, or in other aspects the method can comprise obtaining and analyzing a plurality of aliquots from one or more samples and/or that are obtained under different conditions. For example, one method comprises obtaining two aliquots per sample, wherein the first aliquot is obtained by application of about 50 millibars (e.g., 10-100 millibars, such as 15-95 millibars, 20-90 millibars, 30-80 millibars, or 40-70 millibars) for about 3 minutes (e.g., 1-10 minutes, such as 1.5-8 minutes, 2-7.5 minutes, 2.5-5 minutes, or the like, in some cases it potentially being advantageous to perform the first aliquot extraction for shorter times in this or other contexts, such as 0.25-4 minutes, 0.33-3.5 minutes, 0.5-3 minutes, 0.5-4 minutes, 0.5-5 minutes, 0.5-2.5 minutes, 0.5-2 minutes, 0.75-3 minutes, 0.75-2.5 minutes, 0.75-2 minutes, or other similar time interval), and obtaining a second aliquot by putting the sample under pressure conditions of about 5 millibars (e.g., about 1-10 millibars, about 2-8 millibars, about 3-7 millibars, or the like) for a period of about 10 minutes (such as 5-15 minutes, e.g., 6-12 minutes, 6-10 minutes, 5-9 minutes, 6-9 minutes, 7-9 minutes, 7-10 minutes, or about 7 minutes, about 8 minutes, or about 9 minutes), with the method optionally including a step of crushing/squeezing the sample during one or both aliquots, such as crushing the sample at the start of the first aliquot extraction. The methods of the '921 application were applied to characterize the oil content of formations, but I have discovered that even in an area associated with a single oil deposit or several oil deposits of similar characteristics the release of volatile compounds from such samples can be used to actually indicate the characteristics of the rocks and formation itself, rather than oil content or rather than solely oil content. This information, when applied across a number of samples, results in a rock property "map" of the area, which allows for better guidance of fracking operations or other petroleum production operations, and, accordingly better economic returns in connection with such activities. Of course, while the methods of the invention are of particular relevance to oil production activities they also can be applied to other types of formations and other contexts.

In one respect the invention provides methods for assessing the rock content of a geological formation associated with a petroleum deposit comprising (a) obtaining a sample of rock from at least two samples of rock obtained from different portions of a petroleum deposit-associated geological formation, (b) subjecting the samples to conditions that would release detectable amounts of one or more volatile compounds from the samples, if present in the samples, such as the methods of the '921 application, (c) analyzing the amount of the one or more volatile compounds released from the samples, and (d) corresponding the amount of the one or more released volatile compounds with the compositional content of the samples to assess the rock content of the geological formation. The analysis step can be performed based on relative comparison of samples from two or more locations of the formation, by comparison of the data obtained by the method against predetermined standards for various rock types, or a combination thereof. Typically, the method will comprise comparison of results obtained from different samples from different locations of the formation.

The rock samples can be any suitable type samples and be provided in any suitable number. A typical rock sample that is useful in connection with the invention is petroleum drill cuttings, which are essentially free byproducts of petroleum drilling and which are obtained in the ordinary course of petroleum drilling in large numbers from different portions of an associated petroleum well. As such, a collection of samples comprising, primarily comprising, or consisting of drill cuttings often will represent a large region of a well site, such as an area of at least about 200 feet, more commonly at least about 500 feet, at least about 750 feet, at least about 1000 feet, at least about 1500 feet, at least about 2000 feet, at least about 3000 feet, at least about 4000 feet, at least about 5000 feet, at least about 7500 feet, or even at least about 10000 feet in one or more dimensions, for example the collection may be obtained from an area of at least about 10500 feet in depth (e.g., in the case of a "vertical" petroleum well) or length (e.g., in the case of a "horizontal well"), or even larger areas, such as at least about 11000 feet, at least about 11500 feet, at least about 12000 feet, at least about 12500 feet, at least about 13000 feet, at least about 14000 feet, or at least about 15000 feet in depth or length or more.

An advantageous aspect of the invention is that it can be used to identify differences in rock properties or formation properties in relatively small areas, as discussed above (e.g., an area of about 80 meters or less in one or more directions, an area of about 40 meters or less in one or more directions, an area of about 20 meters or less in one or more directions, an area of about 6 meters or less in one or more directions, or an area of about 3.5 meters or less, or even about 2.5 meters or less, in one or more directions). Another advantageous aspect of the invention is the ability to identify such differences even when such differences are failed to be detected by other means such as gamma ray logs, resistivity logs, and/or visual inspection.

The methods of the invention will typically be performed with a number of samples, such as at least 3 samples from at least 2 or 3 locations; at least 5 samples from at least 3 locations; at least 10 samples from 3 or 5 locations; at least about 20 samples from 2-20 locations; at least about 30 samples from at least 2-30 locations, such as at least 3-15 locations; at least about 40 samples from at least 2-40 locations, such as at least 10-40 locations; at least about 50 samples from about 2-50 locations; at least about 60 samples from at least 2-60 locations; at least about 75 samples from 2-75 locations, such as 3-75 locations; or even at least about 100 samples of rock from 2-100 locations, such as 4-100 locations, for example 10-100 locations, 2-50 locations, 10-50 locations, or, e.g., 4-25 locations. A "location" can be separated by any pre-set distance, usually a distance that will reflect differences in the formation, if present, such as at least about 25 feet, at least 50 feet, at least 100 feet, at least about 150 feet, at least about 200 feet, or at least about 250 feet, such as every 20-200 feet, every 25-250 feet, or every 30-300 feet.

The petroleum drill cuttings can be subjected to processing prior to the volatile compound extraction and analysis aspects of the invention. Commonly, but not necessarily, samples, such as cuttings, to be analyzed in the method, will, at a minimum, be washed and dried prior to being subjected to volatiles extraction. Cuttings or other samples may be sometimes sealed at the site such that there is relatively little loss of materials from the samples during the time between collection and analysis. In another aspect, the cuttings or other samples are exposed to environmental conditions prior to analysis. In an unexpected aspect, the use of samples that have been subjected to environmental conditions rather than stored in a sealed state are preferably used in the method of the invention. While not wishing to be bound by any theory it is expected that the loss of compounds during the time of storage may limit the volatiles that can be extracted from the samples to compounds that are more firmly associated with the samples and, thus, more indicative of the state of the rock environment. Other samples that can be used as alternatives to cuttings may include core samples or other rock samples associated with a geologic formation.

In some embodiments, as noted elsewhere herein, the samples have been subjected to conditions that can cause the release, loss, or degradation of petroleum or petroleum-associated volatiles in the samples, such as through relatively long term storage in environmentally exposed conditions (e.g., storage for at least 1 week, at least 1 month, at least 2 months, at least about 3 months, or longer under unsealed conditions), or by subjecting the samples to active conditions to artificially "age" the samples (causing the loss of petroleum and/or petroleum-associated volatiles content) (e.g., through heating, crushing, chemical treatment, and/or a combination thereof).

The method of rock volatiles analysis described in my prior patent applications hereby incorporated by reference provide methods that can be used for the extraction, capture (trapping), release, and analysis of volatile compounds from materials, including, in particular, petroleum well cuttings. The release of volatile compounds may be achieved by application of any suitable condition or combination of conditions described in these patent applications. Typically, the method comprises releasing one or more volatile compounds by exposing the samples to low vacuum conditions or at least exposing samples to conditions that are known to be suitable for the release of such compounds, if present, from a number of different types of samples.

As already noted, the methods of releasing/extracting, capturing/trapping, and analyzing volatile compounds provided in my prior patent applications can also be used in performing the methods described herein. Thus, in a preferred aspect, the method comprises releasing volatile compounds, for example by application of one or more vacuum pressures, such as those exemplified in my prior patent applications, and then capturing and analyzing the released volatile compounds by the cryogenic trap and/or mass spectrometry analytical methods that are described in my prior patent applications, which may be combined with, for example, sample crushing step(s). The analysis can be any suitable form of analysis, though the use of quantitative analysis for two, three, four, five, six, seven, eight, ten, or more compounds and/or classes of compounds, such as those exemplified in the Figures and Examples (e.g., benzene, naphthalene(s), acetic acid, formic acid, oil saturated water, and/or methane, and the like), will often be advantageous.

In one aspect, as noted elsewhere herein, a "single aliquot" method is used to determine the rock properties of samples. The suitability of single aliquot approaches to such methods reflects just one of the many surprising aspects of the inventive methods provided herein.

In certain embodiments, the compounds targeted for release and analysis may include those which allow for analysis of aromatic content, naphthene content, paraffin content, hydrocarbon content, toluene content, benzene content, oil saturated water content, acetic acid content, formic acid content, methane content, or other similar or related rock content measures which may be used in analyses to indicate reservoir features for mapping purposes or for indication reservoir gas or oil content or reservoir productivity potential.

The results of analyzing released/extracted volatile compounds can be used to effectively map an area of two, three, four, five, six, seven, or more regions of a geologic formation (e.g., 2-20 regions, 2-12 regions, 2-10 regions, such as 2-8 regions, 2-7 regions, or 2-5 regions). Within a group of regions, such as a formation comprising 3, 4, 5 or more regions, there can be a number of regions that are similar in nature.

For example, the method may identify a first region ("region one") having characteristics A, a second region ("region two") having characteristics B, and a third region ("region three") having characteristics A, again, such as where B reflects a fault condition or other rock condition or composition that separates two otherwise similar/substantially identical rock formations. The identification of natural zones of fracture, such as faults, by such an analytical method, for example, represents just one useful application of the method. The application of the method also or alternatively can identify two or more distinct regions in a formation or can be used to confirm the uniformity or substantial uniformity of a formation.

Thus, for example, the invention provides a method in which a formation, such as a well site, is known to be associated with a deposit or set of petroleum deposits having at least substantially similar properties (in terms of grade, chemistry, etc.), such that the detection of different volatiles released from rocks in the formation is reflective of the differences in rock properties of the formation. The identification of two zones of different properties can identify a fault, or identification of three zones of different rock properties, with first and third zones surrounding a second zone which has markedly different properties from the surrounding zone (and either similar or different properties as compared to one another), can be indicative of a fault area, where petroleum production is advantageous. In some cases, the first zone and third zone have different properties from each other, indicating that oil has migrated from the second zone (the fault) into one of the zones. This can arise, for example, when brine has mixed with water in one of the fault-adjacent zones, whereas oil has dominated the other adjacent zone. In such contexts, performance of drilling operations in the fault zone and in the adjacent zone that is indicative of the presence of oil is typically desired, with the exclusion of drilling operations in the brine-rich/water-rich zone, which usually will be associated with the formation of economically less productive, concrete-like, impermeable rock structures.

Once again, a principles of the present invention is that different volatile compound contents and/or chemistries associated with the samples (and/or the lack thereof), particularly when, for example, such samples are associated with a single petroleum deposit or a set of petroleum deposits that have substantially identical/similar characteristics are reflective of differences in the mineral/rock content of such rocks and/or the physical state of such rocks. For example, in one exemplary aspect the results of volatile analysis can indicate that a sample or set of samples exhibits a volatile compound profile that is associated with a rock region that has a relatively high shale content or that the samples are associated with a rock that like shale is resistant to characterization by previously known wire logging techniques. In another aspect, the method can be applied to a rock or a rock sample that would be classified as a carbonate or another rock sample that is not readily susceptible to physical and/or rock content characterization by visual inspection. In still another aspect the method comprises identification of one or more regions that have a relatively high silt content. This can be determined based on comparison with standard results obtained in similar situations. In other cases, as described elsewhere herein comparative analysis of rocks from different regions of a formation also or alternatively is performed to determine the characteristics of the rock and/or other structural aspects of the formation, such as identifying fault regions in the formation.

The geological maps of rock regions in a formation that are obtained by the application of the inventive method can be used to direct oil and/or gas production and/or exploration operations, particularly the placement of lateral and/or horizontal drilling lines and/or the selection of areas for fracking, so as to frac in areas that will produce a desired amount of oil and/or that provide a desired amount of economic return. It will be clear to those of skill in the art that the use of information, such as formation maps, generated by the inventive method does not have to be limited to petroleum exploration and/or drilling but could also be used for other types of mining operations, such as mineral production, or for subterranean construction operations, or for any other operation in which assessing, such as mapping, the geologic properties of a region are useful.

As noted above, in one aspect the method of the invention comprises measuring the toluene to benzene ratio released from rock samples in a formation, such as petroleum drill cuttings from a well. Thus, for example, in one embodiment the invention provides a method of characterizing rock content of a geologic formation, and to use such information for related activities such as directing petroleum drilling operations, comprising (a) obtaining a number of samples of rock from the different portions of a geologic formation, (b) subjecting the rock samples to conditions that cause the release of detectable amounts of benzene and toluene from the rock samples, if present in the rock samples, (c) analyzing the amount of benzene and toluene released from the rock samples, and (d) calculating the ratio of toluene to benzene released from the rock samples to characterize the rock properties of the formation. I have discovered that relatively high toluene-to-benzene ratios, such as a minimum ratio of at least about 4.5 to 1, are indicative of parts of formations that typically have important physical properties, and very often are associated with natural fault formations in the formation. In other aspect, a relative increase in the toluene-to-benzene ratio of at least about 33%, at least about 50%, at least about 75%, at least about 100%, at least about 150%, at least about 200%, at least about 250%, at least about 300% (e.g., about 400%, about 500%, about 600%), or a range composed of such values (e.g., about 33%-about 500%) as compared to the average toluene-to-benzene ratio of other samples in the formation is used to identify areas of interest (e.g., expected faults or fault-associated regions). The alternative method is useful in certain areas where the ordinary toluene-to-benzene ratio of petroleum-associated rocks varies from about 3 to 1, which is a typical average (and, thus, an amount normally not indicative of an area of interest, such as a fault). Using either standard, the information can be used to direct petroleum production operations (e.g., drilling, fracking, and/or other operations) to one or more locations identified as being associated with a desired minimum toluene-to-benzene ratio. In some cases, the minimum toluene-to-benzene ratio is set to at least about 5 to 1 or at least about 6 to 1, rather than about 4.5 to 1. In other cases, the minimum toluene-to-benzene ratio is at least about 7.5 to 1, at least about 9 to 1, at least about 10 to 1, or at least about 12 to 1, or a range such as about 5-about 15 to 1 (e.g., about 6-12 to 1). The extraction of toluene and benzene from rock samples, such as cuttings, can be performed by any suitable method, such as the methods described in WO 2018/11194. In one aspect, the method is performed by subjecting the samples to a single set of conditions to release only one aliquot of volatile compounds from each sample (e.g., the method is performed using a "single aliquot" method such as described therein). The samples can comprise and often will be mostly composed of, if not at least 90%, at least 95%, or more composed of drill cuttings, such as petroleum drill cuttings produced in exploration and/or production wells in the formation. As exemplified and discussed below and elsewhere herein, an advantageous aspect of the invention comprises performing the method in horizontal petroleum wells (wells in which the orientation of the well is horizontal in orientation, i.e., predominately more parallel to the surface of the earth).

In another aspect, the invention provides a method of identifying areas of different rock properties in a petroleum-associated geological formation comprising (a) obtaining a plurality of rock samples obtained from different portions of a geological formation associated with a petroleum deposit having at least substantially uniform properties, (b) subjecting the rock samples to conditions that cause the release of detectable amounts of one or more volatile compounds from the rock samples, if present in the rock samples, (c) analyzing the amount of the one or more volatile compounds released from the rock samples, and (d) determining if there is a minimum difference in the release of at least one of the released volatile compounds, such as a difference of at least about 50% in the amount of at least one of the released volatile compounds obtained from a first sample area from at least one sample obtained from a second sample area (e.g., a difference of at least about 60%, at least about 80%, at least about 125%, at least about 150%, at least about 200%, or at least about 300%, or a range thereof, such as a difference of about 50-about 300% in the amount of one or more released volatile compounds). An advantage of the method is that it can detect differences in rock properties of the formation even when the entirety of the formation has been determined to be associated with a single oil deposit or a number of oil deposits have identical or substantially uniform conditions (e.g., in terms of oil grade, chemistry, etc.). Also or alternatively, an advantage of the method is identification of regions of different rock properties where other commonly used analytical methods, such as gamma ray logs and resistivity logs, provide little or no indication that there is a difference in the characteristics of the rocks in the formation. Thus, for example, the performance of such a method can indicate that there is a minimum difference in the release of volatile compounds from two or more portions of the formation but the gamma ray log data and/or resistivity log data associated with the two or more areas do not reflect a difference of more than about 10%, more than about 15%, more than about 20%, more than about 25%, or more than about 30% (e.g., more than about 50%, more than about 75%, or more than about 100% or even more than about 150%), with respect to each other. Another advantageous aspect of the method is that it can, in some embodiments, be used to identify differences in relatively small areas, such as areas of about 100 meters or less in one or more directions, about 50 meters or less in one or more directions, about 30 meters or less in one or more directions or even small areas (e.g., areas of about 20 meters or less in one or more directions, about 15 meters or less in one or more directions, about 10 meters or less in one or more directions, about 7 meters or less in one or more directions, about 3 meters or less in one or more directions, or even about 2 meters or less in one or more directions).

In yet another aspect, the invention provides methods of identifying areas of different rock properties in a geologic formation associated with an oil deposit comprising (a) obtaining a plurality of rock samples obtained from different portions of a geological formation associated with a petroleum deposit having at least substantially uniform properties, (b) subjecting the rock samples to conditions that cause the loss of petroleum from the rock samples, (c) subjecting the rock samples to conditions that cause the release of detectable amounts of one or more volatile compounds associated with petroleum from the rock samples, if present in the rock samples, (c) analyzing the amount of the one or more petroleum-associated volatile compounds released from the rock samples, wherein the presence of a relatively high concentration of petroleum-associated volatile compounds in the samples is indicative of rock having relatively poor petroleum production properties. Similar to other aspects of the invention, such information can be used to, for example, direct oil production operations, such as drilling operations or fracking operations, in an area associated with having an amount of petroleum-associated volatile compounds that are indicative of favorable conditions for oil production. Similar to the permeability determination methods I have invented and described in WO 2018/11194 this method is counter-intuitive in that the identification of less petroleum-associated compounds in the rock is indicative of more favorable petroleum production capabilities. This is because the retention of petroleum in such rocks after being subjected to conditions in which petroleum materials are typically lost from the samples (either long term exposure to environmental conditions or exposure to "active" conditions such as heating, crushing, and the like) means that the rock has one or more properties that cause the rock to retain the petroleum, rather than release it, indicating that petroleum flow and release from such rock will be relatively poor and less economically rewarding. A key difference with such particular methods described herein with respect to such previously described permeability assessment methods is that the method of these aspects can be performed using a single set of conditions for the release of volatile compounds (e.g., use of single aliquots obtained by the methods described in WO 2018/11194).

As described below the methods of the invention can be advantageously performed to identify differences in the characteristics of rocks to identify differences even when such differences are not detectable by regular visual inspection (with the naked eye).

Included in the exemplary data presented below are characteristics of rock properties, as determined by the analytical methods described herein, which may be indicative of the presence or absence of oil or gas in forms which warrant exploration or which can direct petroleum production operations. Characterized rock properties, alone and in combination with knowledge of the properties and characteristics of oil existing within geological formations as described in the exemplary data to follow, may provide an ability to predict petroleum pay zones (areas of high productivity), increasing operational efficiency and potential return on investments of those in the oil and gas exploration industry.

The data obtained by the application of the method can be combined with other analytical methods described in my prior patent applications, such as assessing rock permeability through rock volatiles analysis, and/or can be combined with other known methods for evaluating oil content/quality, gas content/quality, and/or the characteristics of the geologic formation, such as visual inspection of the rock samples.

EXEMPLARY APPLICATIONS OF THE INVENTION

The following exemplary data, experiments, and results are intended to further illuminate particular aspects of the invention, but this disclosure should not be construed in a manner as limiting the scope of the invention.

Example 1

FIG. 1 shows a log of concentrations of various volatile chemicals obtained by applying a cryogenic mass spectrometer system as described in the '921 application to washed and dried cuttings obtained from a petroleum well. Specifically, the well in question here was a high shale content oil well in which drilling was controlled to be in a single 5-foot-thick (~1.525 meter-thick) geologic unit of rock for a length of about 7,000 feet (~213.36 meters).

Unless otherwise stated in this Example, and the other Examples provided herein, the extraction of volatile compounds as reflected in the various Figures was carried out using the volatile compound extraction, cryogenic trapping, release, and mass spectrometry analysis methods described in the '921 application, typically using a "dual" or "two" aliquot method as described therein; however, it is important to understand that other methods could have been performed, as provided in other portions of the description of the invention, and that one or more parameters applied in this method could have been changed while still providing an effective application of the invention (for example, a "single aliquot" method as described in the '921 application could have been successfully applied as an alternative approach and in some embodiments of the invention the use of a single aliquot method is envisioned).

Also specifically, in this Example and, unless otherwise stated, in the other Examples, two aliquots of volatile compounds were released from samples and analyzed from the tested samples by exposing the tested samples to separate pressure conditions of about 50 millibars and then about 5 millibars and a sample crushing step as described in the '921 application was also employed to aid in the release of volatile compounds from the samples.

In this Example, the cuttings that were analyzed were not sealed at the well site or at any other time prior to being subjected to extraction and analysis.

Figure 2:
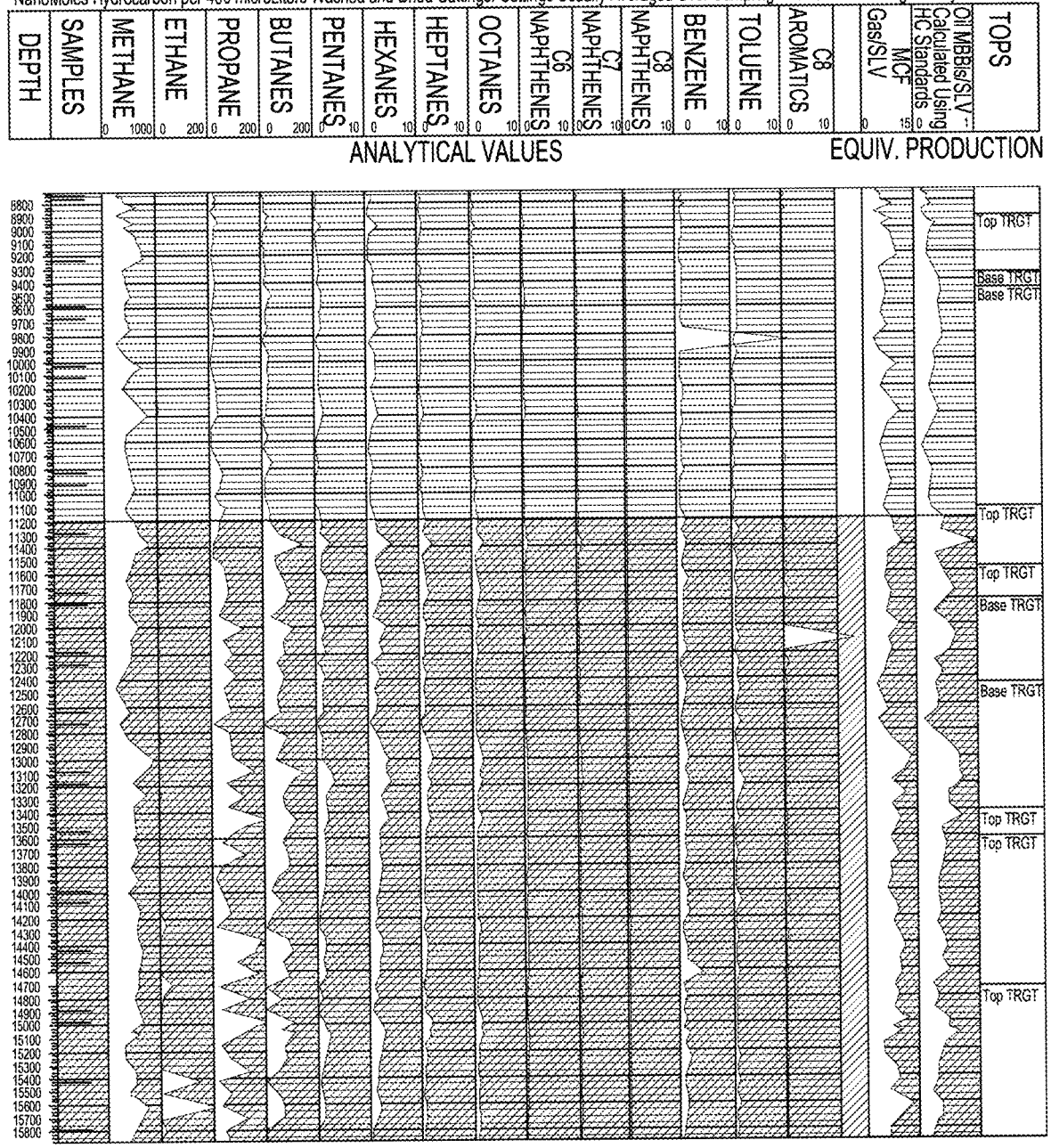

Amounts of the selected volatile compounds extracted, trapped, and analyzed in this experiment from samples obtained at different depths of the above-described well are presented in FIG. 1. Even though only a single unit was drilled, there is an obvious increase of oil and gas in the sample at depths greater than 11,250'. To make this point clearer, this zone of higher oil and gas is shaded in FIG. 2. In FIG. 2 an increased amount of, e.g., C3-C8 hydrocarbons, such as propanes, butanes, hexanes, heptanes, and octanes is observed in this region.

Figure 3:
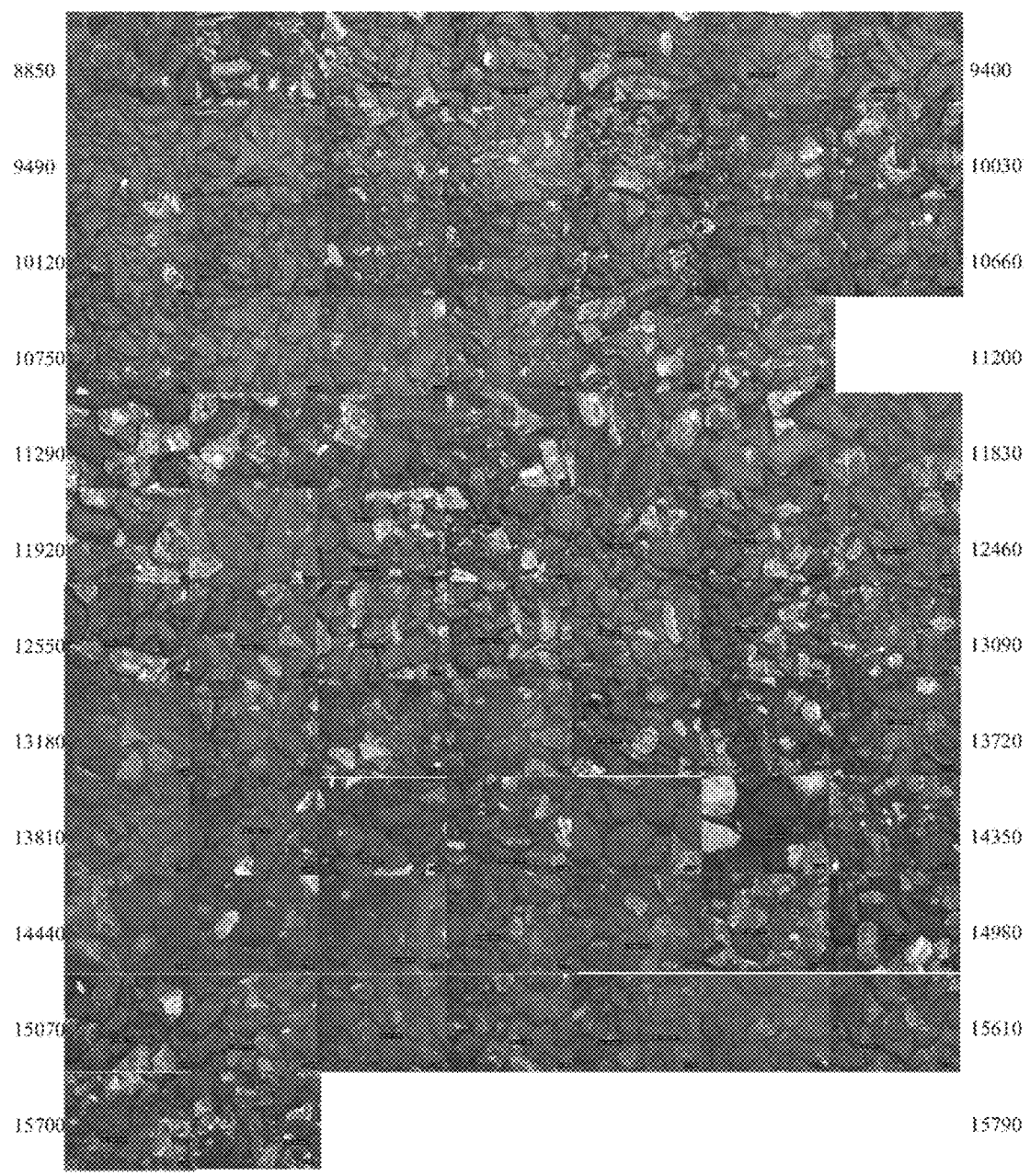

FIG. 3 is a photo-mosaic showing washed and dried petroleum drill cuttings obtained from this horizontal well. Within a row the depths increase from left to right. Vertically, the depths increase from top to bottom. It is clear that cuttings from depths greater than 11250' tended to be lighter in color and show more discrete white patches than cuttings from depths less than 11250'. These visual characteristics provide an indication that the rocks at depths greater than 11250' are relatively higher in silt content (i.e., can be considered "siltier") than those rocks located at depths less than 11250'. The samples from less than 11250', by contrast, have a higher relative shale content (they are "shalier").

Figure 4:
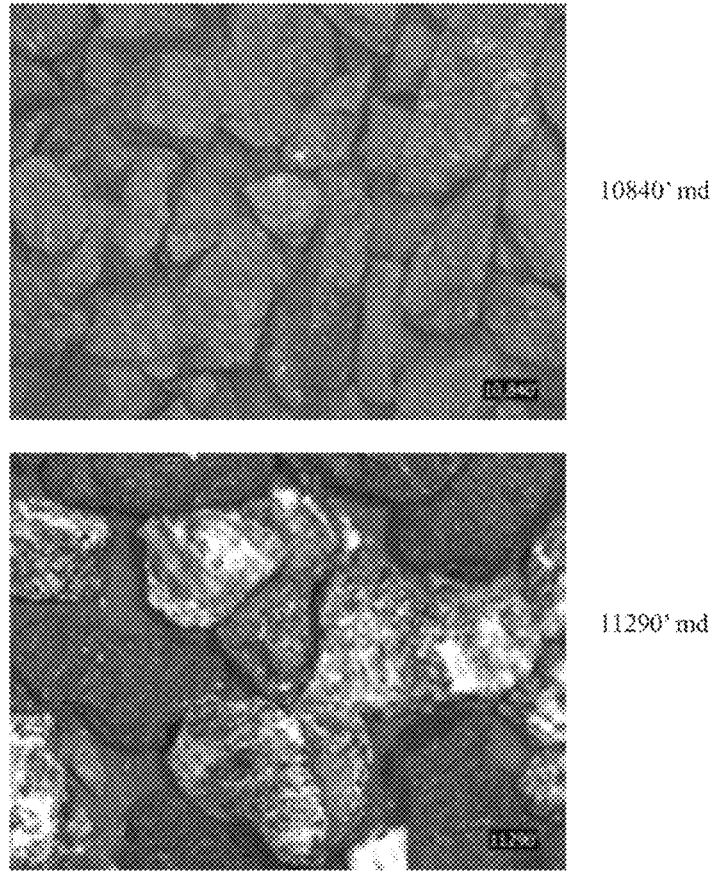
FIG. 4 is a close-up photograph of cuttings from two depths of this same well site.

FIG. 4 shows a close-up photograph of cuttings from two depths, 10840' versus 11290'. It can be seen from FIG. 4, that the 10840' sample is dark and fairly homogenous, while the sample from 11290' is lighter and much more heterogeneous in nature. Siltier shales have larger pore spaces than less silty rock formations, such as shale-rich rocks ("shales"). I believe that it is these differences in the structural/content characteristics of the different rocks in these locations that is a primary cause of the differences in chemical contents seen in FIGS. 1 and 2 (i.e., between the two zones of the well/geologic formation that meet at about 11250').

This Example demonstrates that extraction, trapping, and mass spectrometry identification of volatile compounds contained in rock samples, such as petroleum drill cuttings ("rock volatiles analyses") of cuttings (here, cuttings not sealed at the well) can map out changes in rock properties in this oil shale that can be confirmed visually as corresponding to changes in the content properties of the associated rock. Thus, the method I have invented can be applied with or without visual confirmation as an additional or alternative method of assessing the physical/content characteristics of rocks, such as different portions of a rock formation of interest.

In certain rocks, such as oil shales, and other oil shales and other rock types, visual inspection of the cutting usually does not reveal variation in rock properties. These variations in rock properties are also usually not revealed though analyzing the rock chemistry or mineralogy, as these often remain very similar even for cuttings from rocks having very distinct rock properties. However, rock volatiles analyses as described in this example would be applicable to such materials, such as petroleum drill cuttings obtained from such rocks. Accordingly, my invention of using the volatile compound profile of a rock to characterize the content/structure characteristics of associated rock, especially in cases of rocks in close proximity, provides, in one aspect, a method for evaluating rock content/structure properties where visual inspection fails.

Example 2

This Example and the further Examples provided herein (Examples 3, 4, etc.) are from horizontal wells drilled in carbonates; where, due to their nearly uniform white color, variations of rock properties cannot be readily obtained, if obtained at all, by simple visual observation. Additionally, with the small size of PDC cuttings, macro textures that may reveal important information about content/structural rock properties are not preserved. Also, rock chemistry and mineralogy do not reveal differences in rock properties in these samples as these vary very little in these rocks, even with major changes in physical rock properties. However, the manner in which these washed and dried cuttings samples maintain or lose various oil and gas components is diagnostic, and usually very diagnostic, of changes in rock properties in horizontal wells (across a region of rock containing rock formations of different physical/content characteristics), and vertical wells also.

Figure 5:
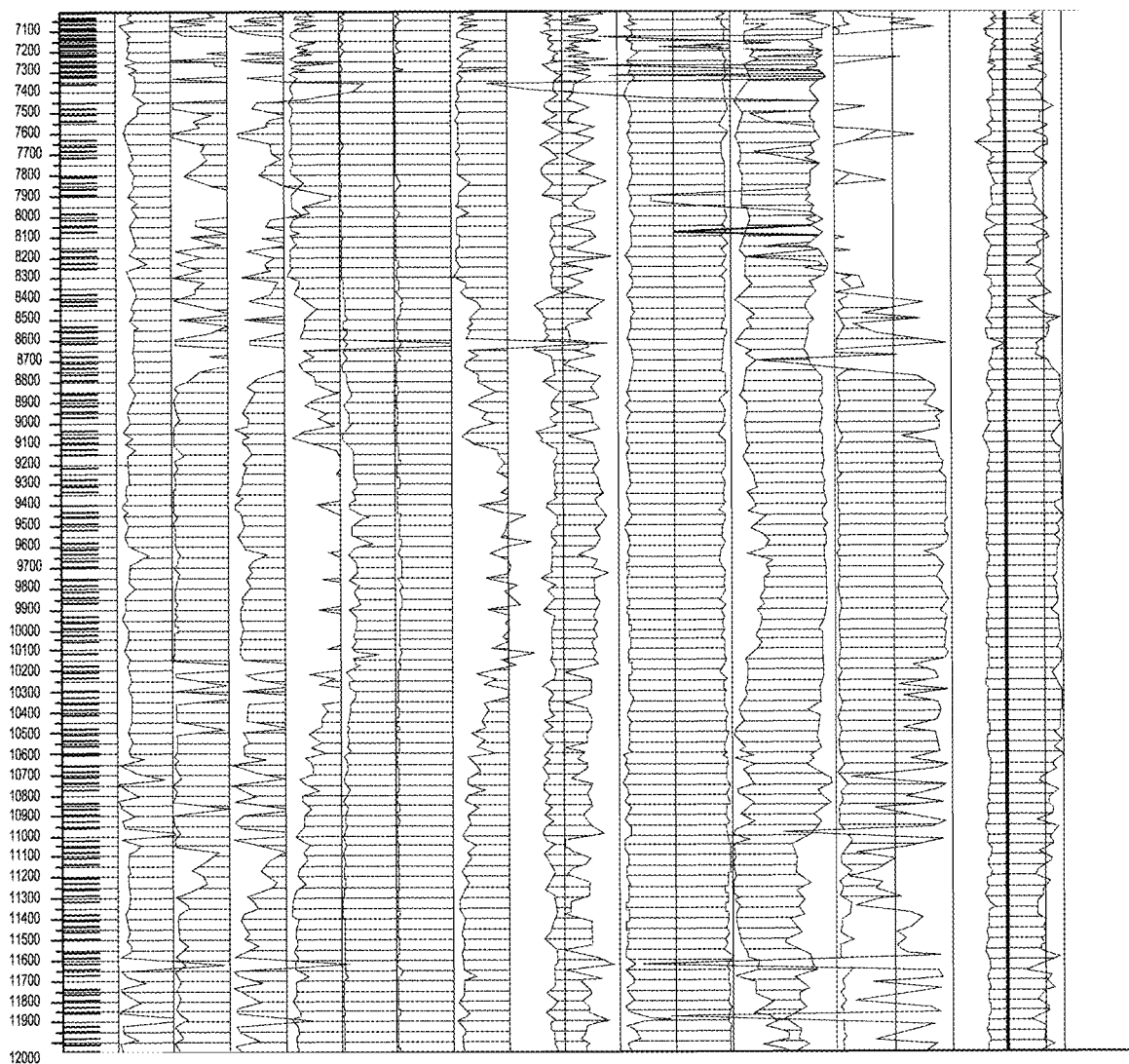
FIG. 5 is another log of volatile chemical compounds obtained for another studied well discussed in the Examples.

FIG. 5 shows one of a log based on the chemical analyses of cuttings from a horizontal well that targeted a single 5' thick carbonate unit. Major relative changes in oil and gas content in the samples were detected as reflected in this Figure. These "changes" (differences) were also reflected in difference in permeability data derived from the same analyses (as described in the '921 application), as well as in the oil saturated water content, toluene/benzene ratio, and the aromatics/(aromatics+naphthenes) ratio for these different formations (as described in the '794 application).

In the subsurface, all, substantially all, or a significant amount of the rocks associated with the well, such as those at issue with respect to this present well, will be associated with ("bathed in") a single deposit or a number of large deposits of oil and/or gas of relatively similar composition throughout the region of the deposit(s), regardless of the number of different types of rocks that are also found in the region. The variations in chemistries associated with different samples of rocks in a region/formation, observed by application of rock volatiles analysis, are caused by, and thus correlate to, variations in rock content/structure properties. These detected differences in properties of rocks correspond to different properties of oil and/or gas production from the relevant formation, such as the petroleum content of the rock formation and/or the amenability of the formation or parts of the formation to successfully produce a target amount of petroleum following fracking. For example, such differences may reflect the ability of some formations/regions to maintain more oil and other formations/regions to retain more gas. In the case of the present Example, there is a relative symmetry to the ends of the graphed data, indicating that the borehole transitioned from one type of rock property strata, penetrated at the beginning of the horizontal well, then to strata having very different rock properties, and after that (at a further/distal location) back to rocks with rock properties similar to those first encountered in this horizontal well.

Carbonate rocks tend to show great variations in rock properties in a lateral sense. This pattern is expected to be indicative of initially drilling a near reef environment, then penetrating a pinnacle reef, and finally re-entering the near reef environment. All indications from this data indicate that the central part of the lateral will produce more oil than either end of the lateral. Thus, this Example demonstrates how the method of the invention can be used to identify rock formations with better petroleum production capability based on the physical/content characteristics of such rocks.

Figure 6:
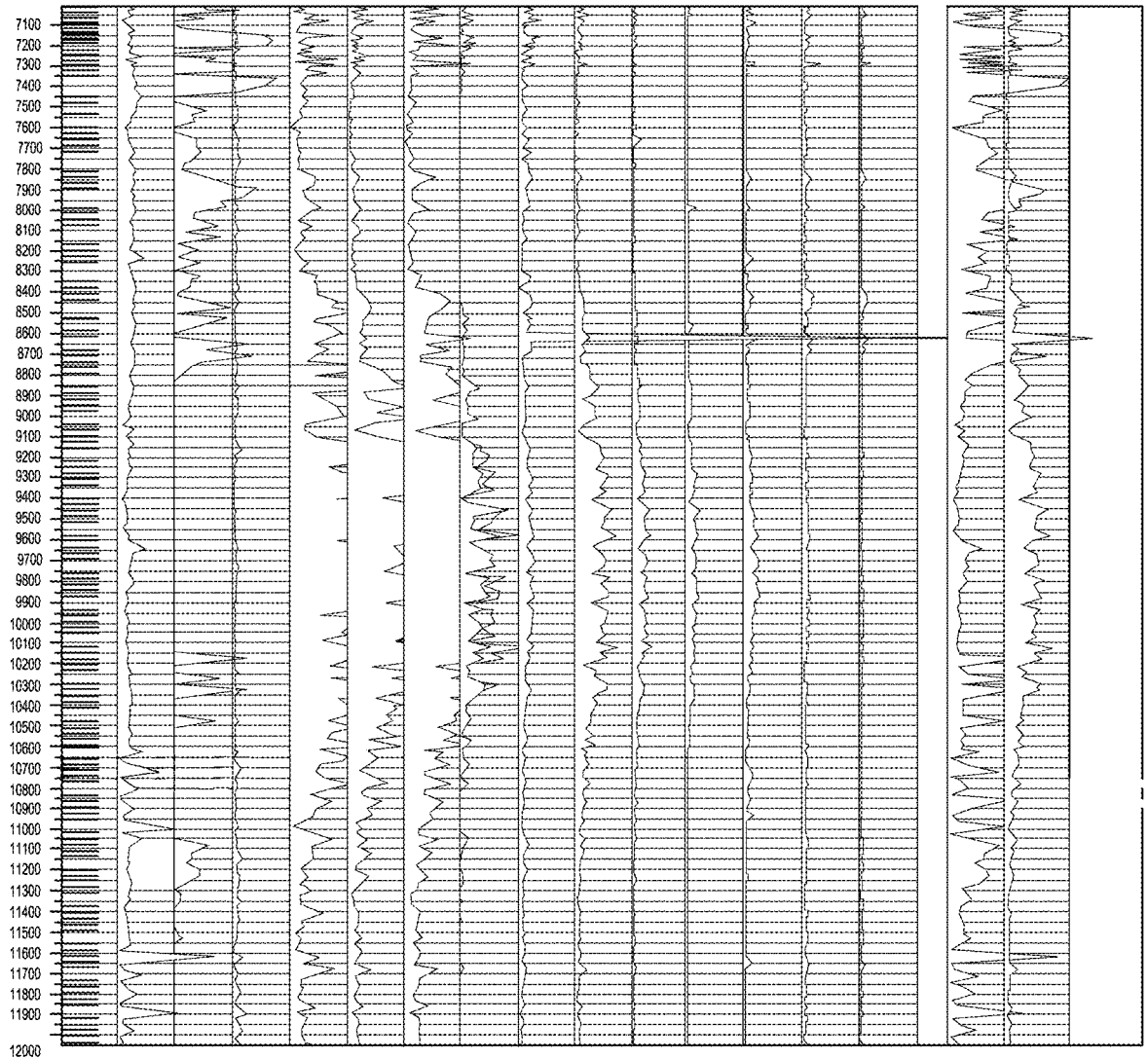
FIG. 6 is a plot of the raw data behind the analysis shown in FIG. 5.

FIG. 6 shows the raw data for the same well. The same pattern of a similar beginning and ending of the lateral in terms of rock composition, as indicated by the profile of volatile compounds observed is shown, but with a distinctly different middle section in terms of oil and gas content is clearly indicated, confirming the observations made above. The step of confirming rock characteristic data, obtained by volatiles analysis, whether through re-analysis of the same raw data, comparison of raw data to manipulated data, and/or through acquiring data through different samples/analyses, is another aspect of the inventive methods provided here.

Analysis of this and subsequent data (not shown) resulted in the determination that the in the middle high oil portion of lateral that both the boundaries are where the well cuts two different faults. Often sites of changes in rock properties occur because of movement on faults which can cause juxtaposition of different rock types, or because of changing from an extensional regime to a compressional regime. The data obtained in this work demonstrates how the inventive method can detect such regions in a geologic formation.

Example 3

Figure 7:
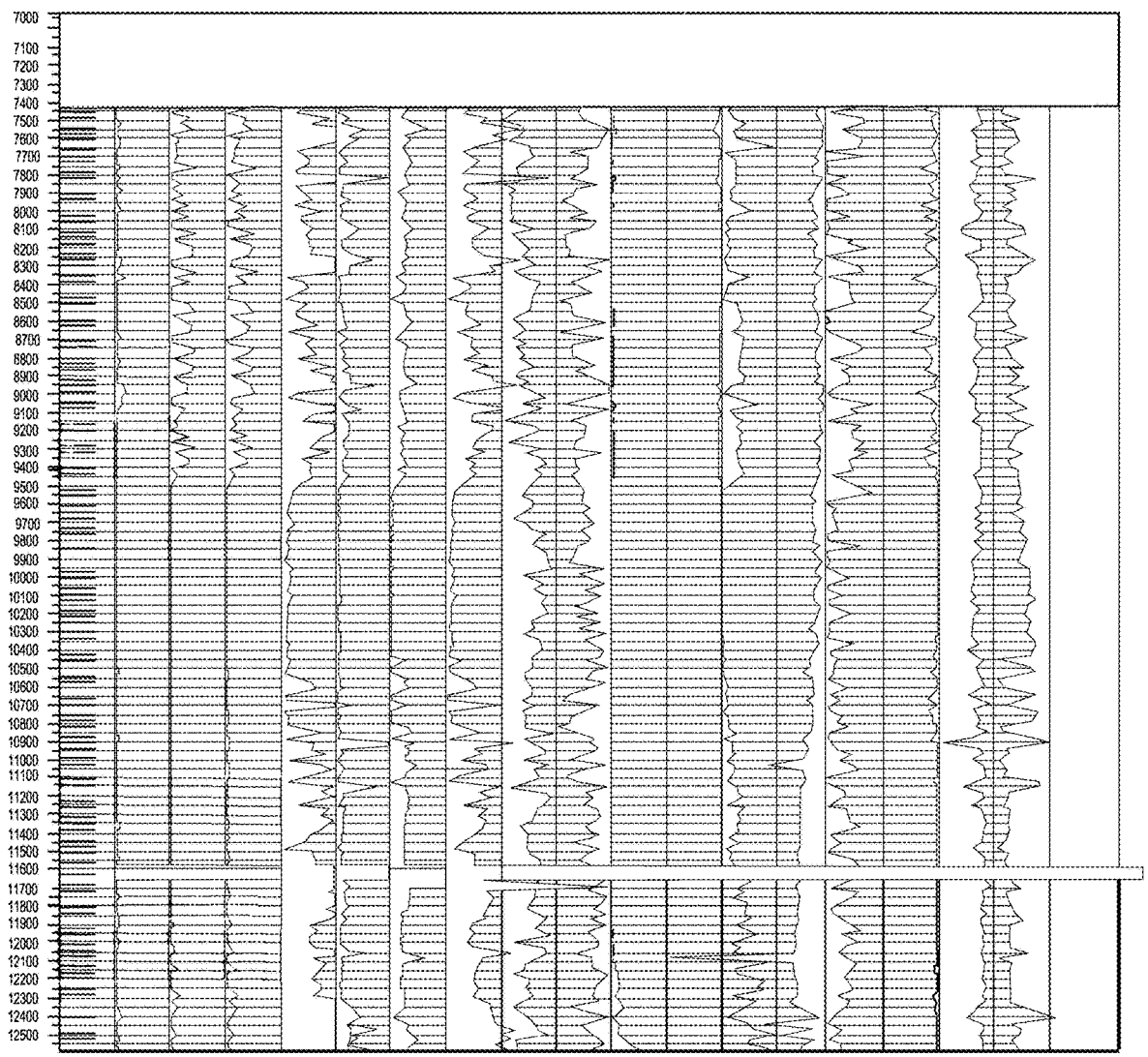
FIG. 7 is another log of volatile chemical compounds obtained for another studied well discussed in the Examples.

Samples were provided from another well and analyzed as discussed in the prior Examples. As reflected in the data obtained by this analysis, which is plotted in FIG. 7, in this well the beginning and ending of the laterals have cuttings containing more oil, whereas the center portion of the lateral has strata that has maintained less oil than the two ends. Mappable variations can also be seen in gas content, Frackability, Oil Saturated water, Toluene/benzene ratio, the (C9+C10)/(C5+ . . . +C10) ratio, and aromatics/(aromatics+naphthenes) ratios. Some of these attributes make the beginning and ending sections look similar, such as oil content, and Oil Saturated Water, and (C9+C10)/(C5+ . . . +C10) ratio, and aromatics/naphthenes; other attributes show there are some distinct differences between the beginning and ending sections, especially gas content, Frackability, and Permeability. Thus, in total these data indicate that three distinct rock property zones exist in the sampled area, although the ending and beginning zones are fairly similar in many respects, especially when compared to the middle section. This Example confirms the ability of the inventive method to map rock properties throughout a formation, and when taken with the results of Example 1 demonstrates that the methods can be applied even in formations having very different compositional characteristics.

Example 4

Figure 8:
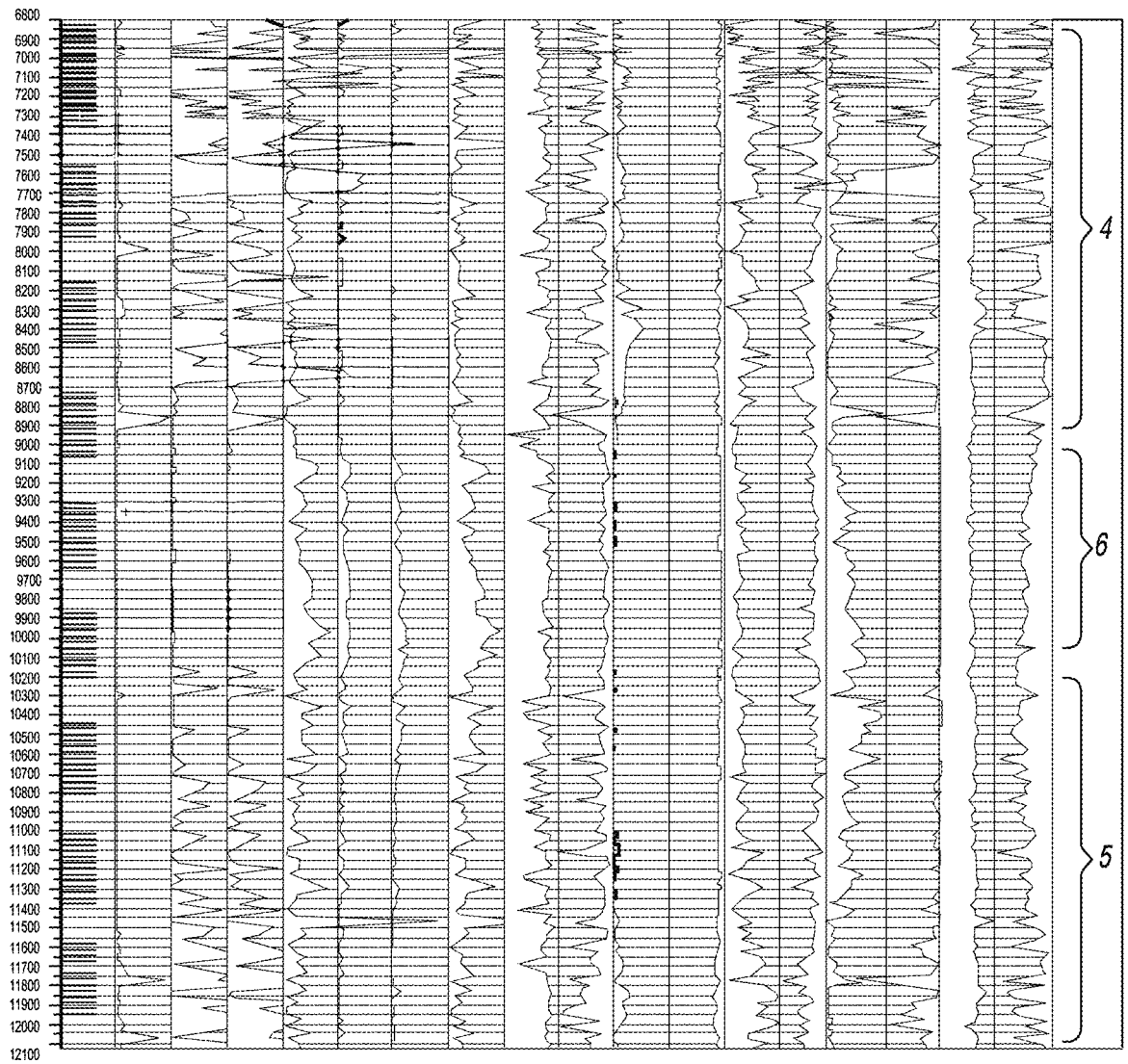
FIG. 8 is another log of volatile chemical compounds obtained for another studied well discussed in the Examples.

Samples from yet another horizontal well were obtained and subjected to rock volatiles analyses as described in connection with the preceding Examples and the results were plotted in FIG. 8. The data obtained from this work and plotted in FIG. 8 shows some noticeable similarities between the beginning (4) and ending (5) sections, and differences with the middle section (6). The beginning and ending sections have higher gas, and higher oil saturated water, and higher and spikier permeabilities, and higher formic acid than does the center section. The center section has higher oil, and a noticeably smoother distribution of permeabilities. However, there is again some difference between the beginning and ending parts of the horizontal well, as the ending section has higher oil than the beginning section. Such differences in the volatile compound properties in an area associated with a substantially uniform oil deposit are indicative of different rock properties in the formation and can be used to direct petroleum production operations.

Example 5

Figure 9:
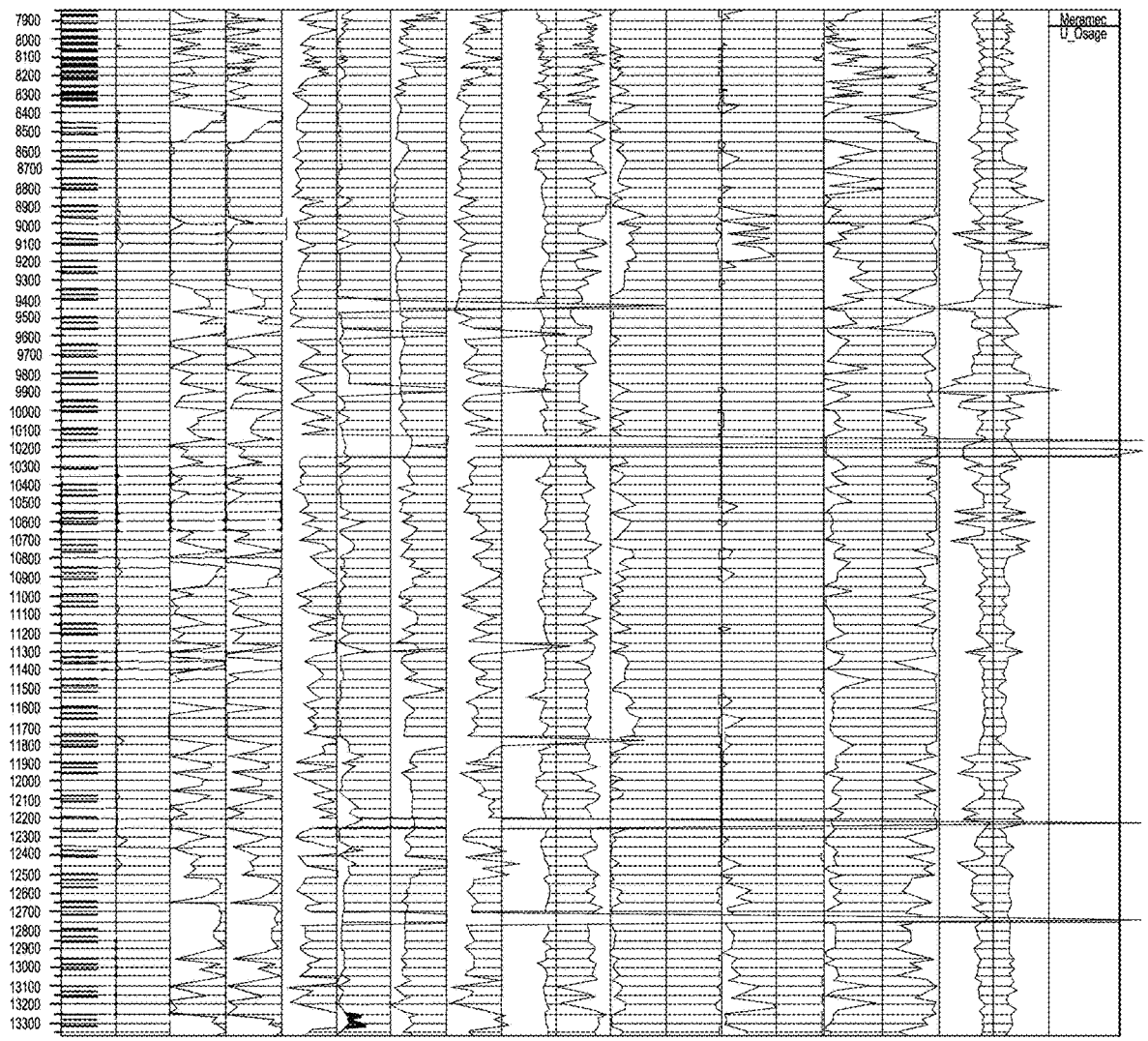
FIG. 9 is another log of volatile chemical compounds obtained for another studied well discussed in the Examples.

FIG. 9 shows data obtained for another carbonate rock-associated horizontal well. As can be seen in FIG. 9 there is distinctly lower oil and gas contents between 8600-9400'.

Below 9400' there are also several spikes of large oil responses that are thought to be zones of large fractures penetrating more oil charged strata above and below the horizontal borehole.

Figure 10:
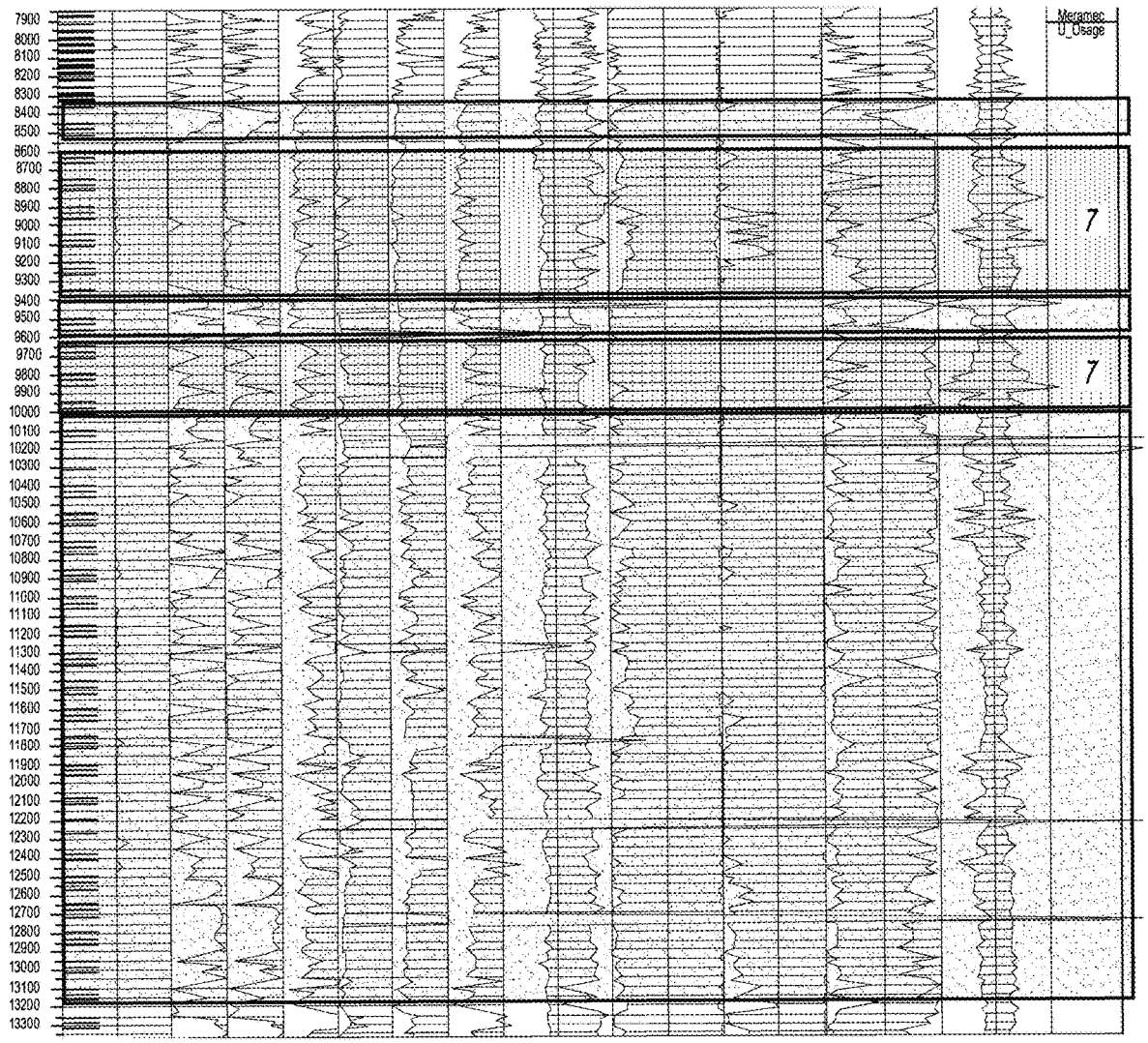
FIG. 10 is a modified plot of the data shown in FIG. 9 emphasizing certain points of the data.

FIG. 10 shows data for the same well as FIG. 9. The shaded areas are zones from the fracked well. The shaded areas marked (7) did not successfully frac. Note the chemically distinct zone from 8600-9400' is a zone that did not frac well.

Application of the inventive mapped out this as a distinct zone in this lateral well and the actual production results confirmed the predictive properties of the results from applying the method. The rock properties of this zone are such that the rocks did not frac.

All of the oil spikes between 10000-13200' indicate large fractures. Also, there are similar large oil spikes in the thin zone between 9400-9600'. These zones of large oil spikes fracked well. The oil spikes are indications of natural fracturing of the rock, which can aid in a successful frac job.

The data shown in FIGS. 9 and 10 show chemical patterns that correlate to fracking success. Applying the inventive methods provided herein have the potential of having major economic impact on fracking horizontal wells. Different frac strategies can be developed for mappable bodies of different rock properties.

Example 6

Figure 11:
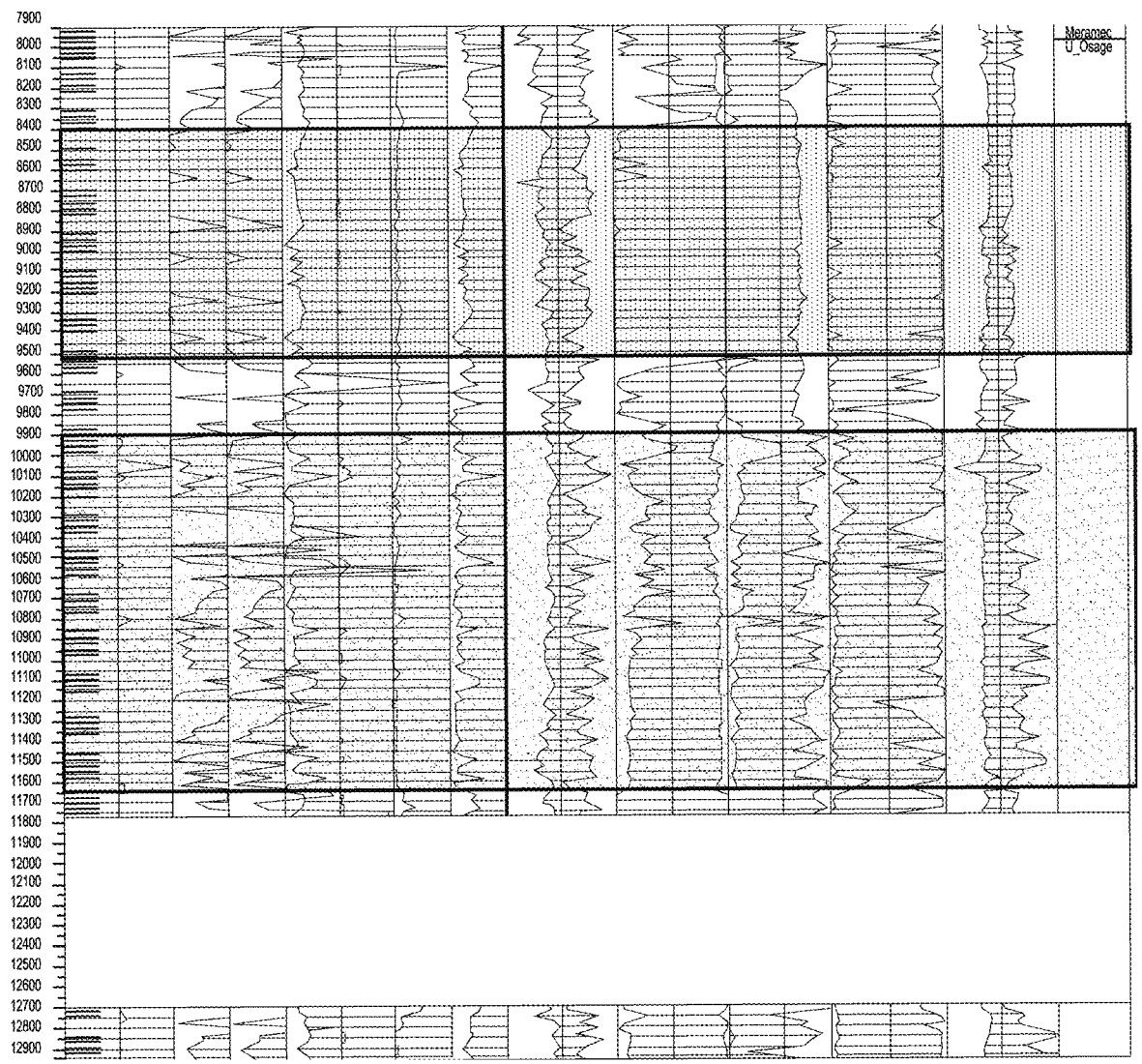
FIG. 11 is another log of volatile chemical compounds obtained for another studied well discussed in the Examples.

FIG. 11 shows data obtained for another well with two distinctly different chemical zones indicated. The white block in the plot reflects an area of the well/formation for which no samples were collected and, accordingly, no released volatile data was obtained. Again, it is important to remember that such distinct chemical zones do not reflect changes in oil and gas compositions in the subsurface; but, rather, are more indicative of how the rocks maintain and lose their oil and gas in the drilling, washing, drying, and storage processes (especially in formations/wells such as those exemplified here in which the entire formation is associated with a substantially uniform oil deposit). The lower shaded section in FIG. 11 is expected to be drilled in the more prospective rock body based on higher Oil Saturated Water, Higher Formic and Acetic Acids, Lower Toluene/Benzene ratios, and lower Aromatic/Naphthenes ratios.

Example 7

Figure 12:
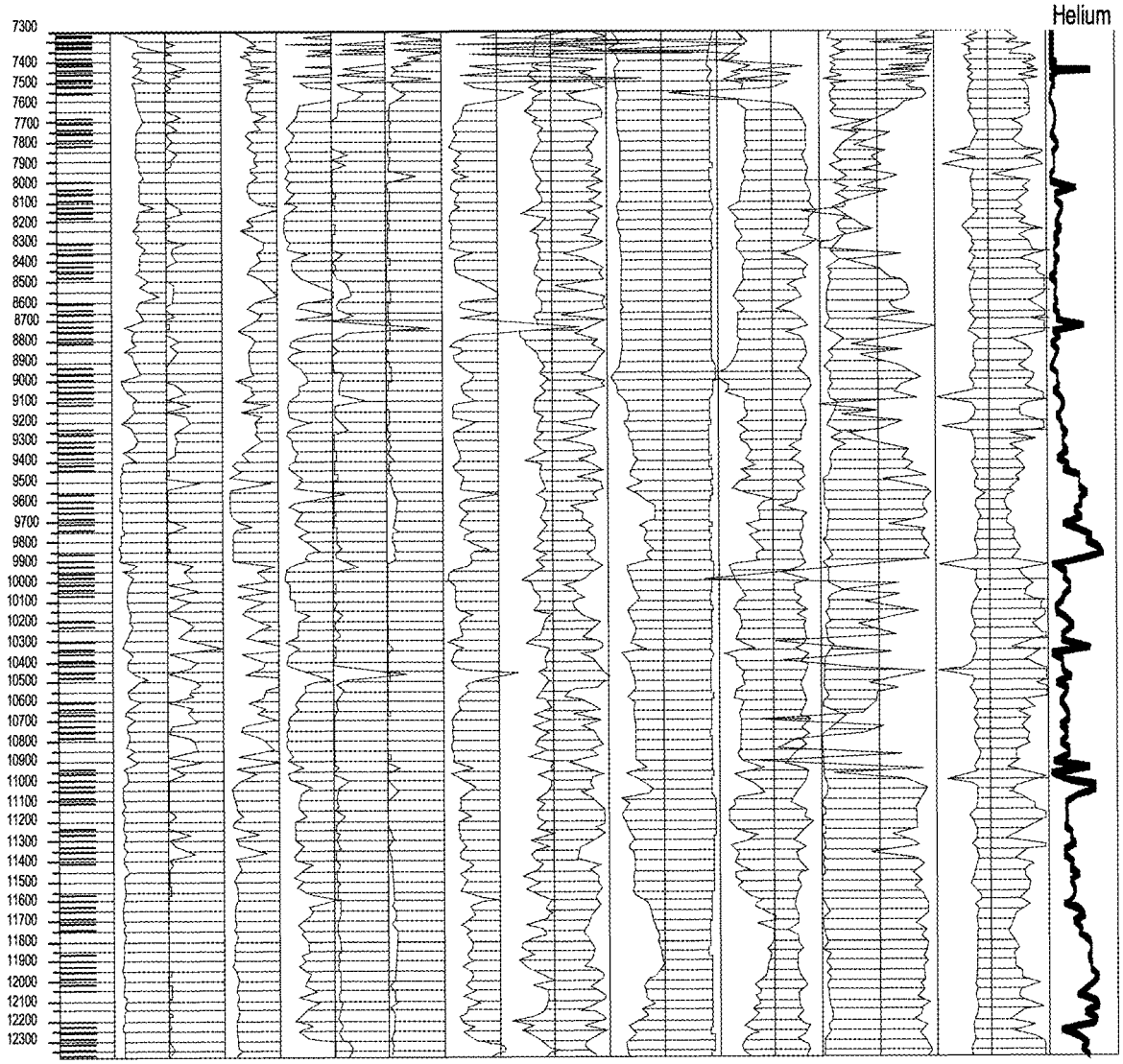
FIG. 12 is another log of volatile chemical compounds obtained for another studied well discussed in the Examples.
Figure 13:
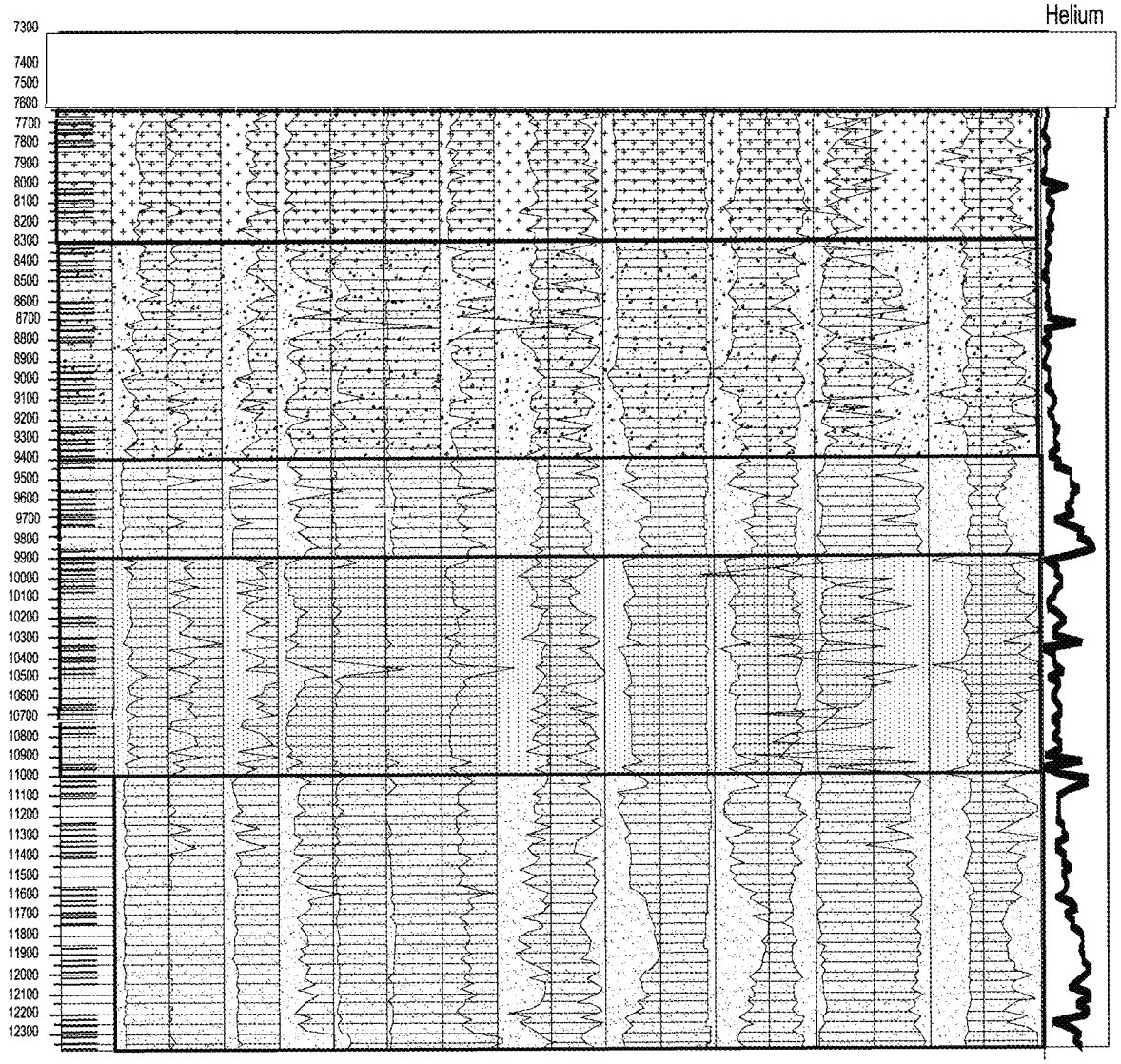
FIG. 13 is a modified plot of the data shown in FIG. 12 emphasizing certain points of the data.

FIG. 12 presents data from yet another distinct well. The data obtained from samples associated with this well is reflective of a more complex formation composition than was observed with respect to the other wells studied in the preceding Examples. In FIG. 13 the data for this horizontal well has been divided into 5 distinct sections, having 4 distinct chemistries. It is believed that this well has penetrated 5 distinct bodies of rock based on their rock properties as revealed by these data, and that 2 of those 5 sections have very similar rock properties.

It is important for successful frac jobs to attempt to frac only rocks of similar rock properties for any given frac stage. A 1 mile lateral usually has about 24 frac stages. If multiple rock types are present in a single frac stage, then the induced fractures and proppant will preferentially enter the weaker rocks, and the oil and gas in the stronger rocks will not be produced. For this and other reasons, application of the inventive methods provided herein are particularly advantageous in mapping rock formations and for guiding fracking operations.

Example 8

FIGS. 14-17 show logs of chemical concentrations obtained by applying a cryogenic mass spectrometer system as described in the '921 application to washed and dried cuttings obtained from yet another distinct horizontal petroleum well.

Amounts of the selected volatile compounds extracted, trapped, and analyzed in this experiment from samples obtained at different depts of the above-described well are presented in FIGS. 14-17.

Figure 14:
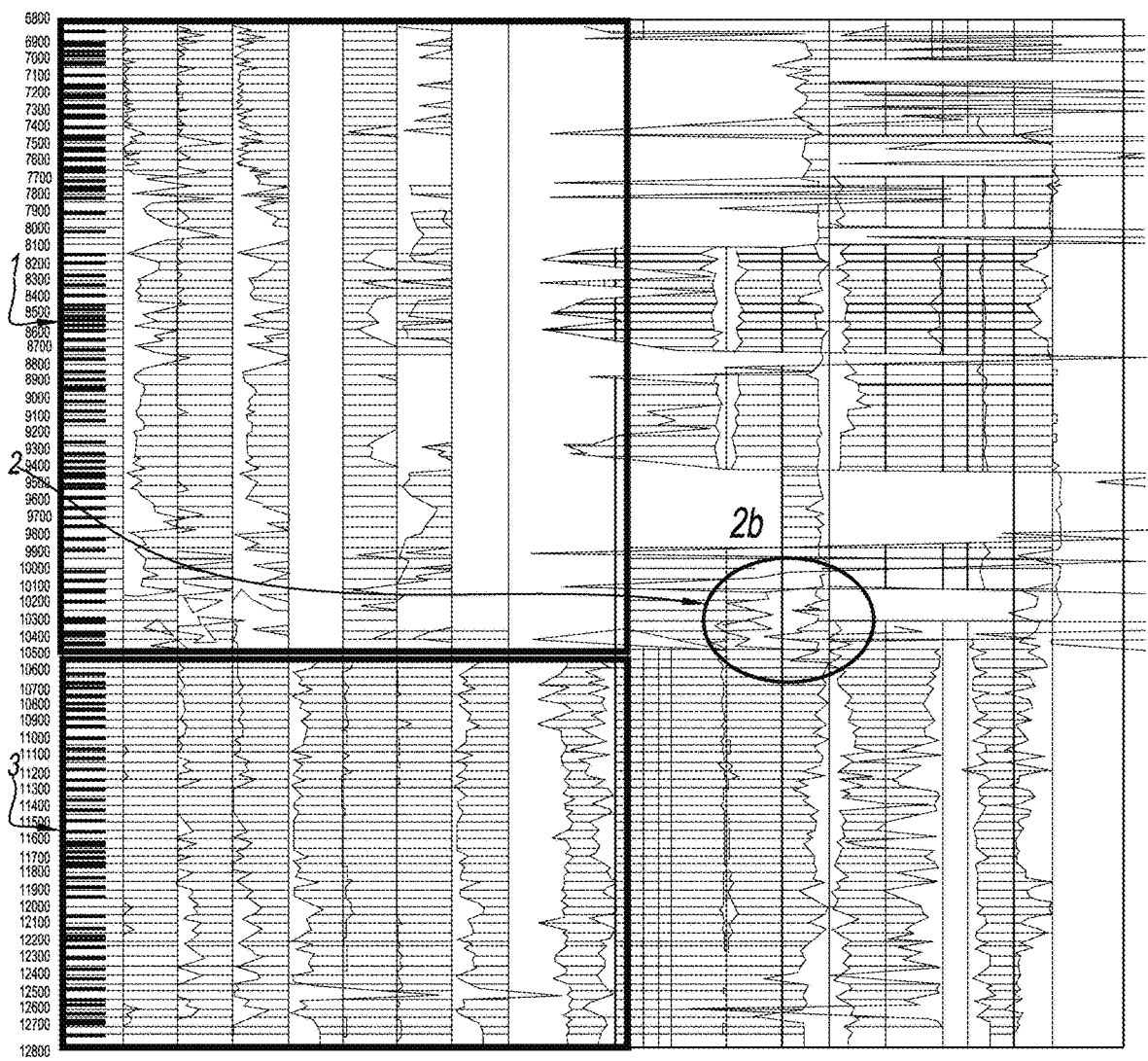
FIG. 14 is another log of volatile chemical compounds obtained for another studied well discussed in the Examples, the log representing data from a first aliquot from the studied well.
Figure 15:
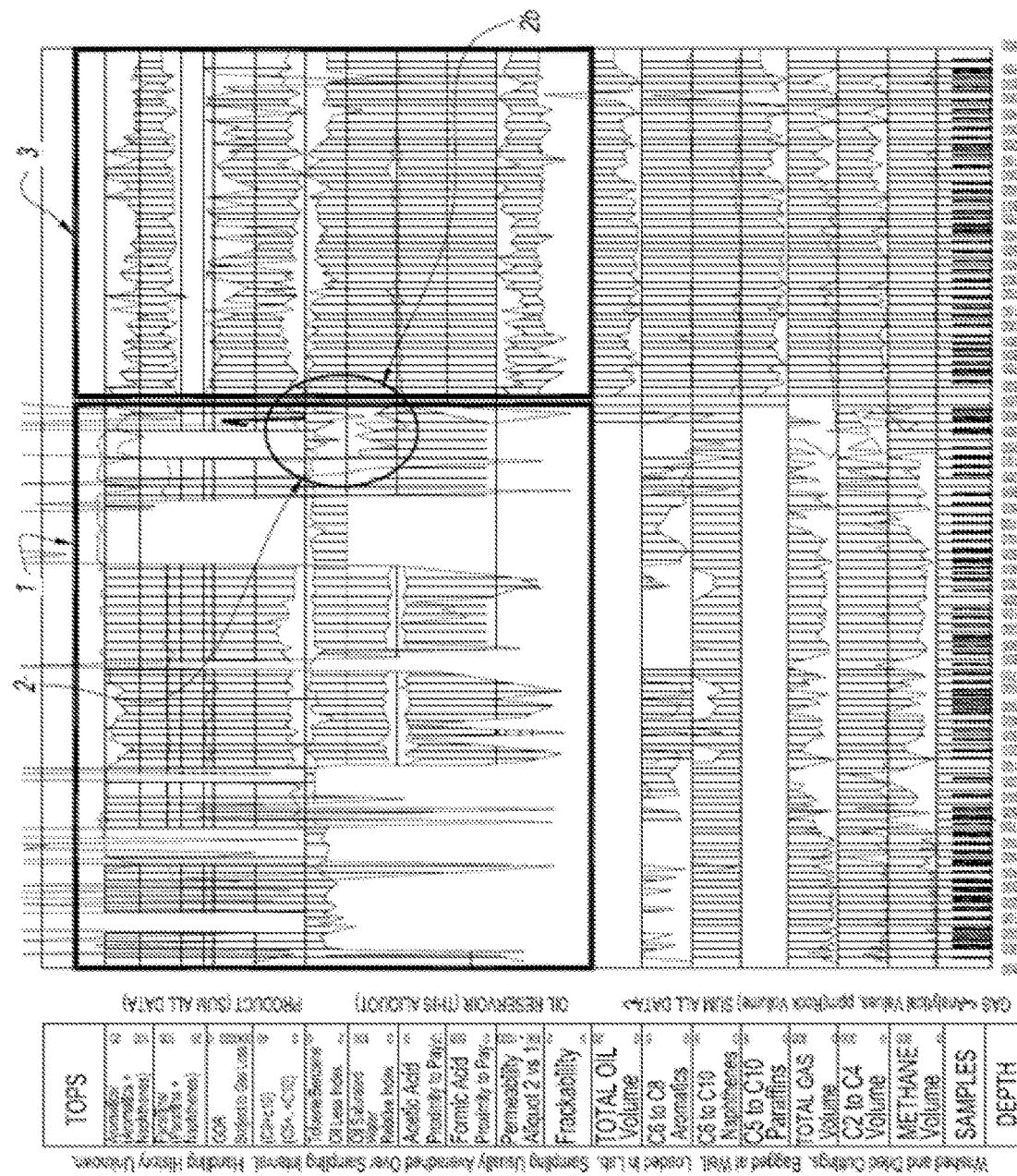
FIG. 15 is the same log of volatile chemical compounds as shown in FIG. 14, re-oriented to emphasize the spatial relationship between features of the well.
Figure 16:
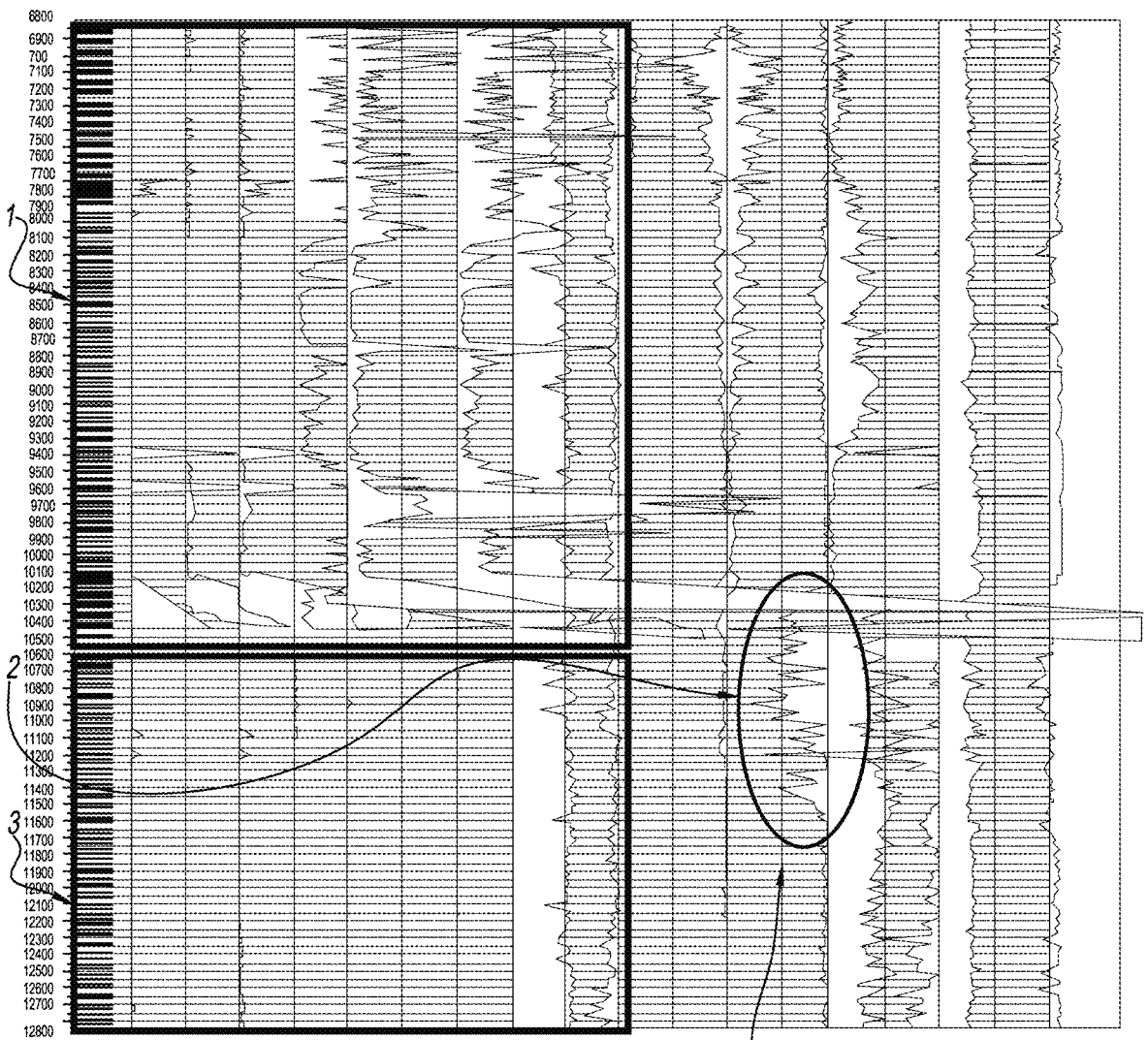
FIG. 16 is another log of volatile chemical compounds obtained for the same studied well as represented in FIG. 14, the log representing data from a second aliquot from this well.
Figure 17:
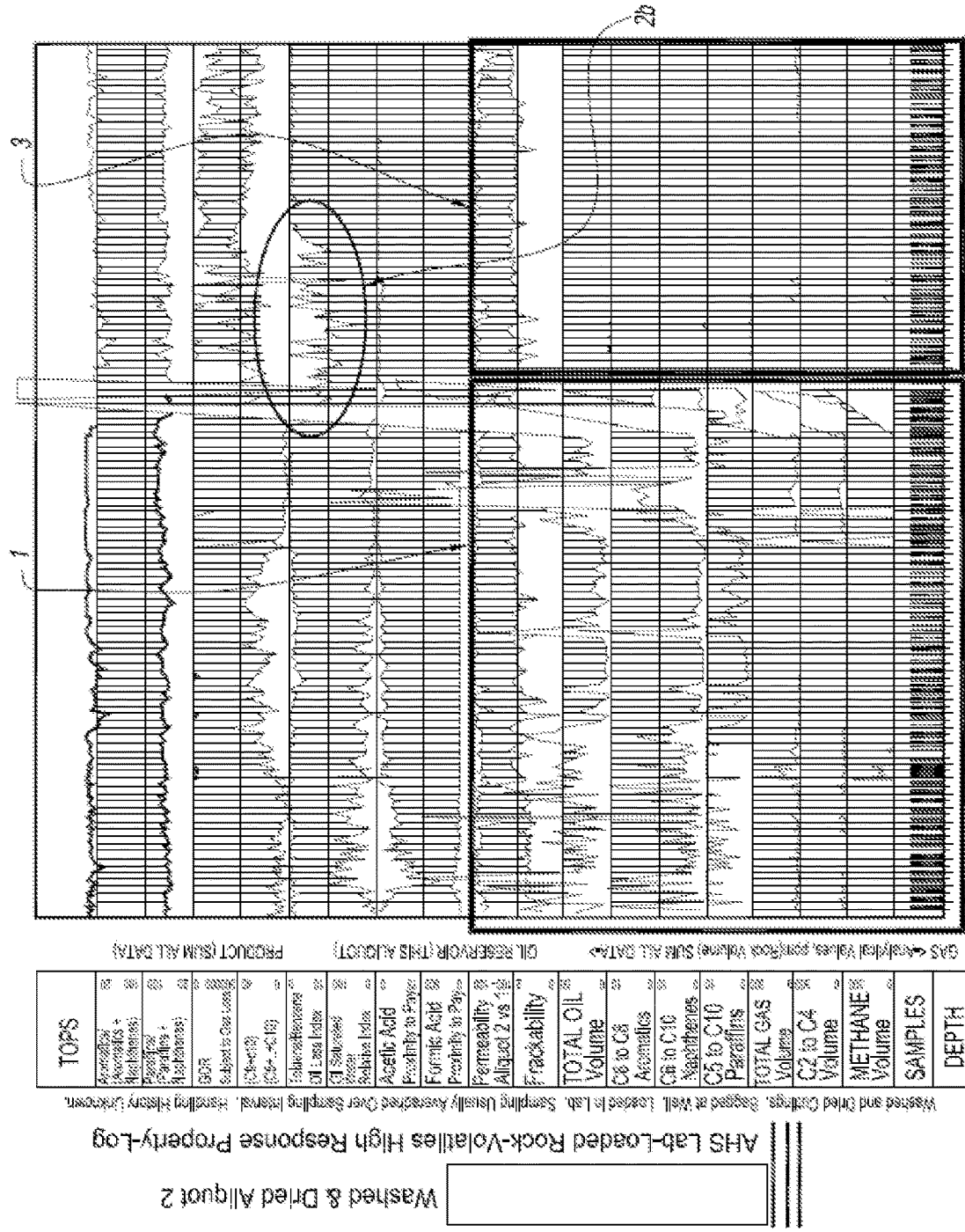
FIG. 17 is the same log of volatile chemical compounds as shown in FIG. 16, re-oriented to emphasize the spatial relationship between features of the well.

FIGS. 14 and 15 represent data from a first aliquot ("first aliquot" indicating a first set of conditions utilized to obtain a first set of data from a set of samples) from the well of this Example. FIGS. 16 and 17 represent data from a second aliquot ("second aliquot" indicating the application of a second set of conditions to the same set of cuttings or samples analyzed in preceding FIGS. 14 and 15 ("first aliquot") and the data resulting from such second set of conditions) of sample from this same well. FIGS. 14 and 15, presenting data from aliquot 1, present the same data; FIG. 15 has simply been rotated so as to show that the upper fault block occurs by the toe of the lateral; that is, the deepest part of the well. The same is true of FIGS. 16 and 17, presenting data from aliquot 2 taken from the same well; each present the same data; FIG. 17 has simply been rotated so as to show that the upper fault block occurs by the toe of the lateral. In the rotated examples, FIGS. 15 and 17, the deepest part of the well is located at the top of the Figure.

The data in this Example exemplify the interpretation of analyzed rock properties and the combination of such data, that is the properties of analyzed cuttings from different spatially distant locations within a well, with data related to the properties and characteristics displayed by oil within geological formations (e.g. the changing chemical profile characteristics of oil as it migrates through geological formations having varying characteristics) to the prediction of preferred reservoir production zones.

The graphical representation of data collected on the first aliquot from the well of this Example is shown in FIG. 14. This same representation of data from FIG. 14 is flipped in FIG. 15, allowing the visualization of the spatial orientation of key well geographical features, keeping in mind that in the rotated Figure, the deepest part of the week is located toward the top of the Figure: upper fault block (reservoir rock above the fault) (1); fault (2), and the predicted preferred reservoir zone (3).

The graphical representation of data collected from a second aliquot from the well of this Example is shown in FIG. 16. This same representation of data from FIG. 16 is flipped in FIG. 17, allowing the visualization of the same spatial orientation of key well geographical features as shown in FIG. 15: upper fault block (reservoir rock above the fault) (1); fault (2), and the predicted preferred reservoir zone (3).

Referring to FIGS. 15-17, in the well of this Example oil migrates along the fault (2). The oil is accompanied by brines, expelled from source rock along with the oil.

The oil migrates into reservoir rock located above the fault (1). The oil enters the reservoir and thus preserves porosity and permeability by displacing the water which was previously present.

The brine enters the lower fault block. This occurs because the brine is heavier than the ancient sea water originally in the pores of rock in the lower fault block. The brine reacts with the ancient sea water, causing mineral precipitation (e.g. cementation). Such precipitation or cementation destroys the reservoir quality of the rock.

The "bad" reservoir rock, or rock which would be identified as not being a preferred drilling target (e.g. tombstone), located in the reservoir rock above the fault (1) shows high levels of oil in analyses. This is because the rock is so tight that the oil does not escape during the process of drilling, transportation of the cuttings to the surface, and sample preparation.

The promising reservoir (3), or the pay zone, is represented by rock which shows very little oil content. This is because it is "good" reservoir rock. It is rock of a higher porosity, higher permeability, and is rock which loses its oil during drilling, transport to the surface, and sample preparation.

Figure 18:
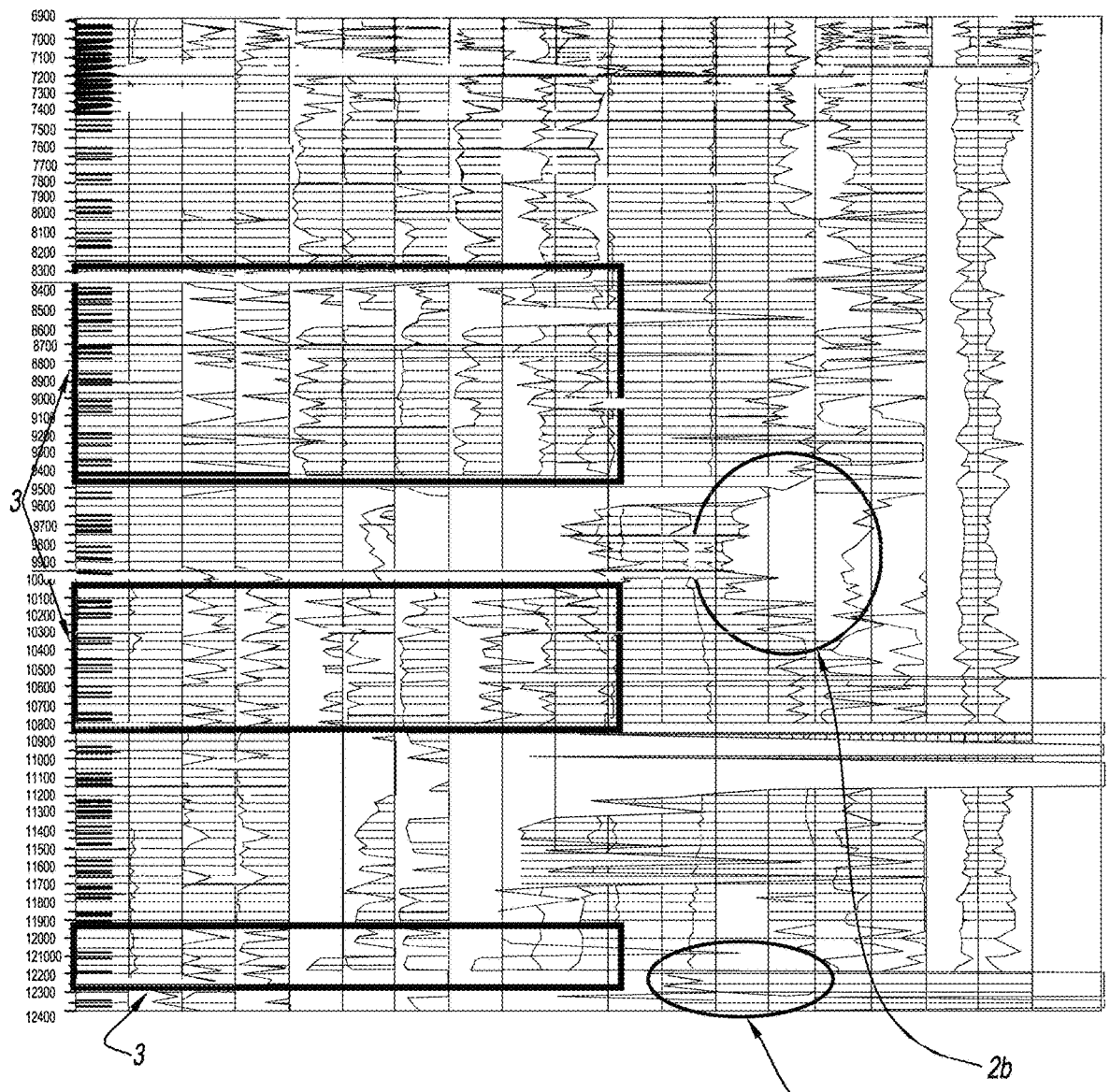
FIG. 18 is a log of another lateral/horizontal well reflecting a high toluene-to-benzene ratio and other volatile compound release information used in the characterization of the well.
Figure 19:
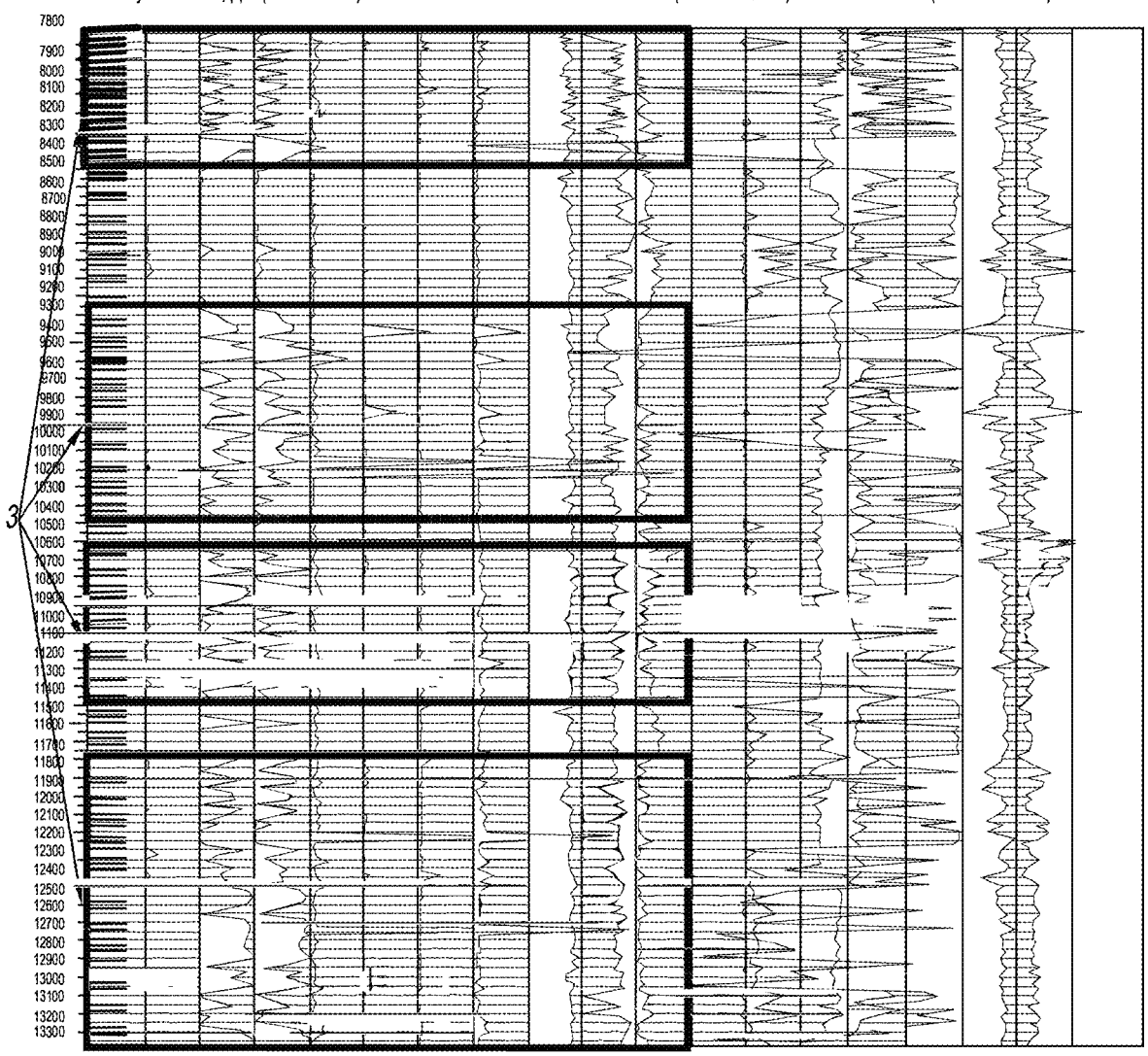
FIG. 19 is a log of a well-performing horizontal petroleum production well showing several areas of predicted production based on application of methods of the invention.

Rock along the fault (2) shows high toluene:benzene ratios as indicated by the circled data labeled 2b FIGS. 15-17. This is also shown in FIGS. 18 and 19 of Examples 9 and 10. Such high ratios indicate a zone of active oil migration. Toluene is a larger molecule than benzene and therefore when oil migrates, it leaves behind more toluene than benzene. High ratio values observed in this part of the data (and corresponding region of the well/formation) are higher than those found in normal oils. The toluene:benzene ratios away from the fault, as represented in other parts of, e.g., FIG. 15 above and below 2b are similar to those observed in typical oils.

The large oil spike clusters observed in the first aliquot data from this well shown in FIG. 14 (and therefore also the rotated version of FIG. 14, FIG. 15), also observed in FIG. 16 and its rotated companion FIG. 17 presenting data from the second aliquot taken from the same well, are likely to be, without intending to be bound by theory, representative of fracture swarms (concentrations or clusters of single fractures within the rock layer).

The characteristics and properties of the rock analyzed in this Example 8 provide the user with the ability to predict and target preferred reservoir zones. It is clear that the data provided by such analysis may contribute to guiding drilling operations in such a manner so as to improve efficiency and improve return on time and monetary investments.

Example 9

Data similar to that described with respect to the preceding Examples was obtained from petroleum drill cuttings obtained from another horizontal/lateral oil well and plotted in FIG. 18. The data shown in FIG. 18 reveals two fault areas (e.g., identified by high toluene-to-benzene ratios) (2b), with oil migration filling adjacent reservoirs (3). Such information can be provided to operators to direct oil production operations, such as placement of additional wells and/or fracs.

Example 10

Additional data similar to that described in the preceding Examples was obtained from petroleum drilling cuttings from another horizontal/lateral oil production well and plotted in FIG. 19. This well had high level of production from throughout most of the plotted region and like other wells included in these Examples was from an area known to be associated with an oil deposit of substantially uniform characteristics. The data as shown in FIG. 19 reflect that several predicted production zones (3) were also identified using the methods described herein including observation of high toluene-to-benzene ratio and identification of other areas of relatively high amounts of some petroleum-associated volatiles identifying changes in rock properties and relatively low amounts of other volatiles indicating a loss of volatiles from the rock samples, which had been stored under unsealed, normal environmental conditions, permitting loss of oil (thus the presence of some high amounts of volatiles were indicative of rocks unlikely to readily release oil).

PRINCIPLES OF CONSTRUCTION

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

What is claimed is:

1. A method of identifying portions of a geologic area likely to have enhanced petroleum production properties comprising (a) obtaining a number of samples of rock from different portions of a geologic area, (b) subjecting the rock samples to conditions that cause the release of one or more volatile substances from the rock samples, the one or more volatile substances comprising a detectable amount of benzene and toluene, wherein most of the one or more volatile substances do not originate from fluid inclusions, (c) analyzing the amount of benzene and toluene in the one or more volatile substances, (d) calculating the ratio of toluene to benzene in the one or more volatile substances, and (e) identifying one or more of the different portions comprising rock samples that release volatile substances that exhibit a minimum toluene-to-benzene ratio of at least 4.5:1.

2. The method of claim 1, wherein the method is performed by subjecting the samples to at least two sets of conditions that cause the release of at least two aliquots of volatile compounds, wherein either or both of the two aliquots comprise toluene and benzene.

3. The method of claim 1, wherein the method comprises subjecting the samples to a pressure of about 10-100 millibars, about 1-10 millibars, or both.

4. The method of claim 3, wherein the method is performed by subjecting the samples to a single set of conditions to release only one aliquot of volatile compounds from each sample.

5. The method of claim 3, wherein the samples analyzed in the method consist essentially of samples that lack relevant fluid inclusions.

6. The method of claim 5, wherein at least 90% of the samples are washed petroleum drill cuttings.

7. The method of claim 6, wherein the minimum toluene-to-benzene ratio is at least about 6 to 1.

8. The method of claim 7, wherein the minimum toluene-to-benzene ratio is at least about 9 to 1.

9. The method of claim 6, wherein the samples are obtained from a horizontal petroleum well within the geologic area and the method comprises directing petroleum drilling or petroleum fracking based on the identification of one or more portions of the horizontal well that exhibit a toluene-to-benzene ratio of at least 4.5:1.

10. The method of claim 9, wherein the geologic area has uniform or substantially uniform properties.

* * * * *